US010267879B2

(12) United States Patent
Yokosawa et al.

(10) Patent No.: US 10,267,879 B2
(45) Date of Patent: Apr. 23, 2019

(54) MEDICAL IMAGE IMAGING DEVICE FOR POSITIONING AN IMAGING SLICE

(75) Inventors: Suguru Yokosawa, Tokyo (JP); Yo Taniguchi, Tokyo (JP); Yoshitaka Bito, Tokyo (JP); Yoshihisa Soutome, Tokyo (JP)

(73) Assignee: HITACHI, LTD., Tokyo (JP)

( * ) Notice: Subject to any disclaimer, the term of this patent is extended or adjusted under 35 U.S.C. 154(b) by 731 days.

(21) Appl. No.: 14/240,441

(22) PCT Filed: Jul. 27, 2012

(86) PCT No.: PCT/JP2012/069242
§ 371 (c)(1),
(2), (4) Date: Feb. 25, 2014

(87) PCT Pub. No.: WO2013/027540
PCT Pub. Date: Feb. 28, 2013

(65) Prior Publication Data
US 2014/0191756 A1  Jul. 10, 2014

(30) Foreign Application Priority Data
Aug. 25, 2011 (JP) ................. 2011-184161

(51) Int. Cl.
*G01R 33/54* (2006.01)
*G01R 33/483* (2006.01)
(Continued)

(52) U.S. Cl.
CPC .......... *G01R 33/483* (2013.01); *A61B 5/0037* (2013.01); *A61B 5/055* (2013.01); *G01R 33/543* (2013.01); *A61B 5/0042* (2013.01)

(58) Field of Classification Search
CPC .. G01R 33/30; G01R 33/543; G01R 33/4833; G01R 33/483; A61B 5/055; A61B 5/4566; A61B 5/0037; A61B 5/0042
See application file for complete search history.

(56) References Cited

U.S. PATENT DOCUMENTS

2003/0139660 A1* 7/2003 Tatebayashi .......... A61B 5/055
600/407
2005/0088177 A1  4/2005 Schreck et al.
(Continued)

FOREIGN PATENT DOCUMENTS

JP  4-319335  11/1992
JP  6-114033  4/1994
(Continued)

OTHER PUBLICATIONS

S. Yokosawa et al., Automated Scan Plane Planning for Brain MRI using 2D Scout Images, Proc. Intl. Soc. Mag. Reson. Med 18, May 1, 2010, #3136.
(Continued)

*Primary Examiner* — David M. Gray
*Assistant Examiner* — Laura Roth
(74) *Attorney, Agent, or Firm* — Baker Botts L.L.P.

(57) ABSTRACT

A technique in a medical imaging apparatus being capable of setting any plane in three-dimensional space as an imaging slice is provided, allowing an automatically-set imaging slice to be configured to suit user's preferences, and determine a position of the imaging slice being configured, with respect to an imaging target subject automatically with a high degree of accuracy. Reference information for specifying the imaging slice, set by the user for each imaging site, is associated with the anatomical feature of the imaging site, so as to generate an imaging slice parameter. Upon actual imaging, the imaging slice parameter and the anatomical feature of the imaging target subject obtained by scout imaging are used to determine the imaging slice position of the imaging target subject.

19 Claims, 14 Drawing Sheets

(51) Int. Cl.
    *A61B 5/055*    (2006.01)
    *A61B 5/00*    (2006.01)

(56) References Cited

U.S. PATENT DOCUMENTS

| | | | |
|---|---|---|---|
| 2008/0009709 A1 | 1/2008 | Guehring et al. | |
| 2009/0190813 A1* | 7/2009 | Qu | G06K 9/6207 |
| | | | 382/130 |
| 2012/0093385 A1* | 4/2012 | Yokosawa | A61B 5/0037 |
| | | | 382/131 |
| 2012/0283546 A1* | 11/2012 | Zuehlsdorff | A61B 5/055 |
| | | | 600/410 |
| 2013/0106905 A1* | 5/2013 | Sunaga | A61B 5/055 |
| | | | 345/619 |
| 2013/0322727 A1* | 12/2013 | Goto | G06T 1/0007 |
| | | | 382/132 |

FOREIGN PATENT DOCUMENTS

| | | |
|---|---|---|
| JP | 06-114033 | 4/1994 |
| JP | 2005-125099 | 5/2005 |
| JP | 2007-319689 | 12/2007 |
| JP | 2009-279218 | 12/2009 |
| JP | 2010051726 A * | 3/2010 |

OTHER PUBLICATIONS

Laurent Itti, et al. Automatic Scan Prescription for Brain MRI, Magnetic Resonance in Medicine 45, 2001, pp. 486-494.
Yokosawa, et al., "Automated Scan Plane Planning for Brain MRI using 2D Scout Images", Proc. Intl. Soc. Reson. Med., vol. 18:1 (May 2010).

\* cited by examiner

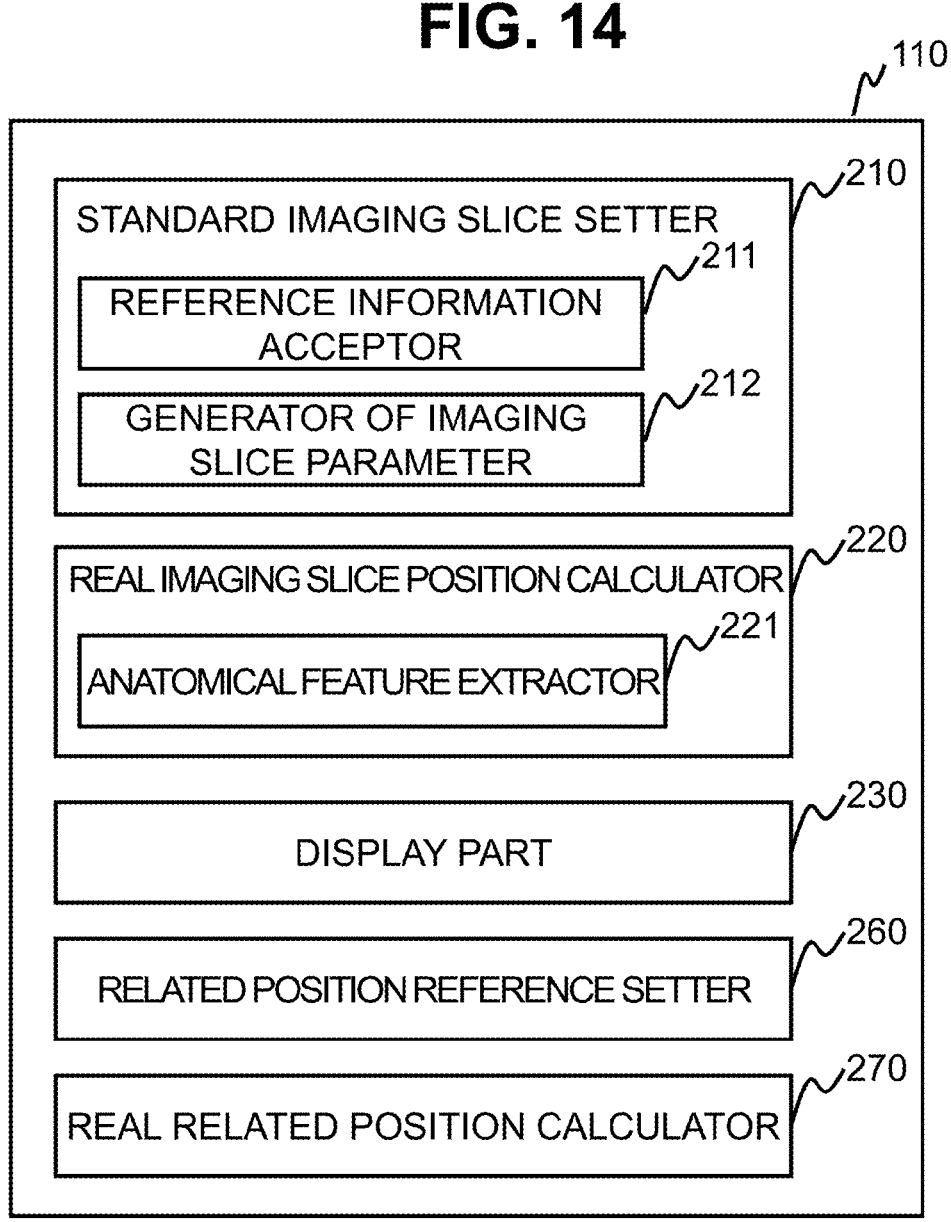

MEDICAL IMAGE IMAGING DEVICE FOR POSITIONING AN IMAGING SLICE

TECHNICAL FIELD

The present invention relates to a technique for positioning an imaging slice in an examination that employs a medical imaging apparatus such as a magnetic resonance imaging apparatus.

BACKGROUND ART

There is a medical diagnostic imaging apparatus that takes an image of a slice at a desired position and inclination in three-dimensional space, so as to use the image for diagnosis. In particular, a magnetic resonance imaging (hereinafter, referred to as MRI) apparatus is a medical diagnostic imaging apparatus, which mainly uses a nuclear magnetic resonance phenomenon of a proton, and it has no restriction on an imaging site, allowing any slice to be imaged non-invasively.

In general, a slice gradient magnetic field is applied to a subject placed in a static magnetic field, and simultaneously, a radio frequency magnetic field having a specific frequency is applied, thereby exciting nuclear magnetization within the slice that is targeted for imaging. Next, the nuclear magnetization excited by applying a phase encoding gradient magnetic field and a readout gradient magnetic field is provided with planar positional information, and a nuclear magnetic resonance signal generated by the nuclear magnetization is measured. Measurement of the nuclear magnetic resonance signal is performed repeatedly until filling up the measurement space referred to as k-space. The signals filled in the k-space are transformed to an image according to an inverse Fourier transform. Controlling gradient coils in three systems respectively associated with orthogonal triaxial directions allows the gradient direction of the magnetic field of each gradient magnetic field to be set in any direction in the three-dimensional space. In the MRI apparatus, spacial control of this gradient magnetic field implements imaging of any slice.

In the medical diagnostic imaging apparatus such as the MRI apparatus that is capable of taking an image of any slice, it is necessary to set an imaging slice of the diagnostic image and the position thereof at the time of examination. Generally, in the examination using the MRI apparatus, an imaging referred to as scout imaging is executed for setting the imaging position, and an imaging slice of the diagnostic image and the position thereof (imaging slice position) are set on the scout image being acquired.

A standard of the imaging slice position is established depending on an imaging target site and disease, and it is set assuming an anatomical organizational structure on the scout image as a landmark. In general, an imaging range displayed on the scout image is manually operated via a user interface, thereby setting the imaging slice position. Setting of the imaging slice position depends on the posture upon placing the subject and an individual difference of the anatomical organizational structure, and therefore it is necessary to configure the settings, every time taking an image of a new subject.

There is suggested a method for setting the imaging slice position automatically, in order to enhance the operability upon setting the imaging slice position. As a method of the automatic setting, for example, there is a technique to register in advance several types of diagnostic planes for deciding the imaging slice position automatically, together with a decision algorithm thereof, allowing user's selection (e.g., see Patent Document 1). In addition, there is a technique for storing an imaging range as a standard protocol, the range being set on a typical image (standard image), and adjusting the range so as to fit for individual subject (e.g., see Patent Document 2). On this occasion, the adjustment is performed according to mapping, by utilizing a transform matrix. Furthermore, there is a technique to perform the automatic setting by the use of image recognition (e.g., see Non Patent Document 1). It is expected that the automatization may produce effects such as not only operability enhancement, but also enhancement of imaging slice reproducibility at the time of follow-up examination.

PRIOR ART DOCUMENT

Patent Document

Patent Document 1
Japanese Unexamined Patent Application Publication No. 4-319335
Patent Document 2
Japanese Unexamined Patent Application Publication No. 2005-125099

Non Patent Document

Non Patent Document 1
Itti L, Chang L, Ernst T, "Automated Scan Prescription for Brain MRI", Magnetic Resonance in Medicine, 2001 45; p. 486-494

DISCLOSURE OF THE INVENTION

Problem to be solved by the Invention

The method described in the Non Patent Document 1 predetermines the diagnostic imaging slice position being automatically set, and therefore it is not possible to alter this automatically-configured imaging slice position so as to suit user's preferences. In the method described in the Patent Document 1, a user selects the algorithm being prepared in advance, thereby allowing the imaging slice position to be designated automatically, but the diagnostic planes are restricted to those being prepared, resulting in a low degree of flexibility.

On the other hand, the method as described in the Patent Document 2 analyzes statistical data sets, and this allows setting of a imaging slice position to suit user's preferences. However, multiple data items are necessary for setting the imaging slice position, and the setting is extremely cumbersome. In addition, this method requires a process for converting each data-set including imaging slice position information to an imaging slice position in a standard image, and a process for converting the imaging slice position on the standard image to an imaging slice position on an image of the subject being an imaging target. In general, the imaging slice position is determined using a certain limited tissue as a landmark, but in those conversion processes, individual difference information of all over the image is reflected. Therefore, an individual difference that is not related to a criteria for setting the imaging slice position may exert influence, deteriorating a degree of accuracy of the imaging slice position.

The present invention has been made in view of the aforementioned situations, and an object of the present invention is to provide a technique in a medical imaging apparatus such as an MRI apparatus that is able to set any plane in three-dimensional space as an imaging slice, the technique allowing an automatically-set imaging slice to be configured in such a manner as suiting user's preferences, and determining a position of the imaging slice being configured, with respect to an imaging target subject, automatically with a high degree of accuracy.

Means to Solve the Problem

According to the present invention, an imaging slice parameter is generated, by establishing association between reference information specifying an imaging slice being set by a user with respect to each imaging site, and an anatomical feature of the imaging site. In actual time of imaging, the imaging slice parameter and the anatomical feature of an imaging target subject being obtained by scout imaging, are used to determine an imaging slice position of the imaging target subject.

Specifically, a medical imaging apparatus is provided, capable of imaging any slice in three-dimensional space, including a standard imaging slice setter for setting as a standard imaging slice, an imaging slice being recommended depending on an imaging site, and generating an imaging slice parameter from the standard imaging slice being set, a real imaging slice position calculator for calculating a real imaging slice position as a position of the standard imaging slice in an imaging target subject, and a display part for displaying to a user, the real imaging slice position being calculated, as a recommended imaging slice, wherein the real imaging slice position calculator is provided with an anatomical feature extractor for extracting an anatomical feature of the imaging target subject on a scout image, and calculates the real imaging slice position by using the imaging slice parameter and the anatomical feature, and the standard imaging slice setter is provided with a reference information acceptor for accepting a setting of reference information as a reference for specifying the standard imaging slice, and a generator of imaging slice parameter for generating the imaging slice parameter, by associating the reference information with the anatomical feature that is extractable by the anatomical feature extractor.

Effect of the Invention

According to the present invention, a medical imaging apparatus, such as an MRI apparatus being capable of setting any plane in three-dimensional space as an imaging slice, allows an automatically-set imaging slice to be configured to suit user's preferences, and a position of the imaging slice being configured, with respect to an imaging target subject, to be determined automatically with a high degree of accuracy.

BRIEF DESCRIPTION OF DRAWINGS

FIG. 14 is a functional block diagram of the computer according to the fourth embodiment.

MODES FOR CARRYING OUT THE INVENTION

<First Embodiment>

Hereinafter, a first embodiment to which the present invention is applied will be explained. In the entire drawings for explaining the embodiments of the present invention, constituents having the same function are labeled the same, and tedious explanations shall not be made. In the following, a magnetic resonance imaging (MRI) apparatus will be taken as an example of the medical imaging apparatus that is capable of imaging any slice in three-dimensional space, in order to explain the present embodiment.

As discussed above, the MRI apparatus of the present embodiment applies a radio frequency magnetic field on a subject placed in a static magnetic field, excites nuclear magnetization within the subject, and measures a nuclear magnetic resonance signal (echo signal) being generated. On this occasion, a gradient magnetic field is applied to provide positional information to the measured magnetic resonance signal, thereby creating an image (imaging).

Figure 1:
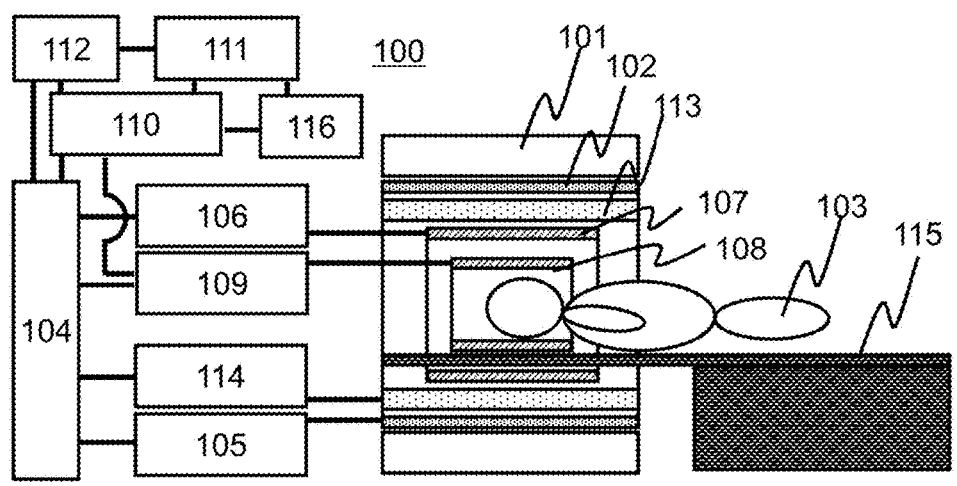
FIG. 1 is a block diagram showing an MRI apparatus according to the first embodiment.

FIG. 1 is a block diagram showing a typical MRI apparatus 100 according to the present embodiment to implement the MRI apparatus as described above. This MRI device is provided with a magnet 101 for generating a static magnetic field, a gradient coil 102 for generating a gradient magnetic field, an RF coil 107 for irradiating a subject (living body) 103 with a radio frequency magnetic field pulse (hereinafter, referred to as RF pulse), an RF probe 108 for detecting an echo signal generated from the subject 103, and a bed (table) 115 for placing the subject (e.g., living body) 103 within the static magnetic field space generated by the magnet 101.

The MRI apparatus 100 of the present embodiment is further provided with a gradient magnetic field power supply 105 for driving the gradient coil 102, a radio frequency magnetic field generator 106 for driving the RF coil 107, a receiver 109 for receiving the echo signal detected by the RF probe 108, a sequencer 104 for sending a command to the gradient magnetic field power supply 105 and the radio frequency magnetic field generator 106 so as to generate the gradient magnetic field and the radio frequency magnetic field, respectively, together with setting a nuclear magnetic resonance frequency as a detection criteria to the receiver 109, a computer to apply signal processing to the signal being detected, a monitor 111 for displaying a processing result performed in the computer 110, a storage device 112 for holding a result of the processing, and an input device 116 for accepting an instruction from a user. The storage device 112 further holds various data necessary for the processing in the computer 110.

The MRI apparatus 100 may also be provided with a shim coil 113, and a shim power supply 114 for driving the shim coil 113, when it is necessary to adjust a degree of homogeneity of the static magnetic field. The shim coil 113 is made up of multiple channels, and generates additional magnetic field by the current supplied from the shim power supply 114, so as to correct inhomogeneity of the static magnetic field. The sequencer 104 controls the current flowing in each of the channels constituting the shim coil 113, upon adjusting the degree of homogeneity of the static magnetic field.

In the MRI apparatus 100 having the configuration as described above, under the control of the sequencer 104, an RF pulse is applied to the subject 103 via the RF coil 107, and the gradient coil 102 applies a gradient magnetic field pulse for providing the echo signal with positional information such as a slice selection and phase encoding. The RF probe 108 receives a signal produced from the subject 103, the signal being detected is transmitted to the computer 110, and it is subjected to a signal processing such as reconstructing an image. It is to be noted that the storage device 112 may store not only a result of the signal processing but also the signal itself being detected, an imaging condition, and the like, as needed.

The computer 110 performs not only the signal processing for processing the received signal, but also controls the entire operations, and the like, of the MRI apparatus 100. By way of example, the computer provides an instruction to the sequencer 104 so that each part operates at a timing and intensity being programmed in advance, and controls the operation of each of the parts constituting the MRI apparatus 100 to perform measurement. Among the programs as described above, a program particularly describing the timing and intensity of the radio frequency magnetic field, the gradient magnetic field, and the signal receiving is referred to as a pulse sequence.

The MRI apparatus 100 controls the timing and intensity of the radio frequency magnetic field, and the gradient magnetic field, which are set in the pulse sequence, thereby enabling imaging of any imaging slice of the imaging target subject. In general, a position of the imaging slice in the imaging target subject is determined and reflected on the pulse sequence, so as to take a desired imaging slice.

Furthermore, the computer 110 of the present embodiment controls the user interface such as the input device 116 and the monitor 111, and performs user interface processing that includes to present a processing result to a user, and to accept an input from the user. In addition, the computer processes the echo signal acquired in the MRI apparatus 100 and reconstructs an image. Alternatively, the computer processes the echo signal, calculates a control values necessary for imaging, such as a center frequency and RF irradiation intensity, and transmits the control values to the sequencer 104.

Figure 2:
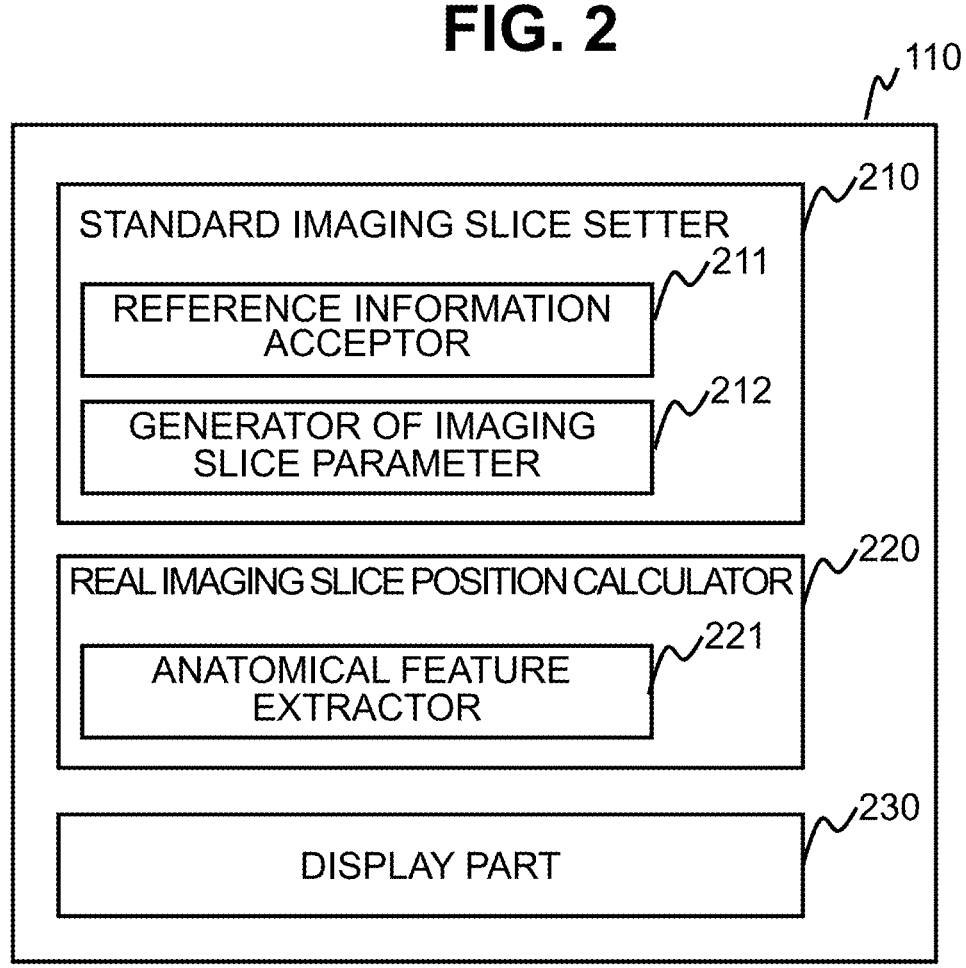
FIG. 2 is a functional block diagram showing a computer according to the first embodiment.

The computer 110 of the present embodiment is capable of designating a recommended imaging slice for each imaging site, in such a manner as suiting user's preferences, and reproduces the designated imaging slice with a high degree of accuracy on the imaging target subject when real imaging is performed. In order to implement this configuration, as shown in FIG. 2, the computer 110 of the present embodiment is provided with a standard imaging slice setter 210 for setting a recommended imaging slice depending on the imaging site as a standard imaging slice, and generating an imaging slice parameter from the standard imaging slice being set, a real imaging slice position calculator 220 for calculating a real imaging slice position being the imaging slice position in the real imaging, as the position of the standard imaging slice in the imaging target subject, and a display part 230 for displaying to a user the real imaging slice position being calculated, as the recommended imaging slice position.

Here, the standard imaging slice is an imaging slice being specified by the anatomical feature of the imaging site, and the slice is set in advance for each imaging site, irrespective of the subject. By way of example, if it is a head region, the imaging slice may correspond to a midsagittal plane, OM line or AP-AC line connecting a nasal root and a lower portion of nasal bridge, a transverse plane along the horizontal plane of Germany, and the like. If it is a lumbar vertebra region, the imaging slice may be a sagittal plane assuming the centrum as a center, and a transverse plane being parallel to the interspinal discs. If it is a knee region, the imaging slice may be a coronal plane being parallel to the line connecting the medial condyle of femur and the lateral condyle of femur and being vertical to the articular facet, a sagittal plane being vertical to the line connecting the medial condyle of femur and the lateral condyle of femur on the coronal plane, etc. If it is a shoulder region, the imaging slice may be a coronal plane being parallel to the supraspinous muscle, a sagittal plane being vertical to the line connecting the bone head and the scapula on the coronal plane, etc. If it is a heart region, the imaging slice may be a sagittal plane along the long axis of the left ventricle, and a transverse plane along the short axis thereof.

As for the anatomical feature, by way of example, it may relate to the median line, head contour, brain contour, corpus callosum, corpus callosum, bridge, brain stem, pituitary gland, and clivus, if the imaging site is the head region; the spinal nerves, interspinal discs, and vertebra, if the imaging site is the spine; positions of the medial condyle of femur, lateral condyle of femur, thighbone, and shinbone, a line connecting the medial condyle of femur and lateral condyle of femur, the articular facet between the thighbone and the shinbone, if the imaging site is the knee; positions of the supraspinous muscle, bone head, scapula, acromion, and clavicle, a line being parallel to the supraspinous muscle, a line along the humerus, a tangent line of the articular facet between the bone head and the scapula, and line connecting the bone head and the scapula, if the imaging site is the shoulder. It is to be noted that in the present embodiment, the anatomical feature extractable by the real imaging slice position calculator 220 is used.

The real imaging slice position calculator 220 of the present embodiment executes scout imaging on the imaging site in the imaging target subject 103, and on the data being acquired, a position of the standard imaging slice in the imaging target subject 103 (real imaging slice position) is calculated, the standard imaging slice being set by the standard imaging slice setter 210.

The real imaging slice position calculator 220 of the present embodiment is provided with an anatomical feature extractor 221 for extracting an anatomical feature on the scout image of the imaging site of the imaging target subject 103. Then, the real imaging slice position calculator 220 calculates the real imaging slice position of the imaging target subject, by using the imaging slice parameter generated by the standard imaging slice setter 210 and the anatomical feature being extracted.

The real imaging slice position calculator 220 of the present embodiment calculates the real imaging slice position, according to an imaging slice position calculation algorithm that is registered in the storage device 112 in advance. In calculating the real imaging slice position, the anatomical feature extractor 221 extracts the anatomical feature according to this imaging slice position calculation algorithm. It is to be noted here that information that specifies the anatomical feature being extractable by the imaging slice position calculation algorithm, is determined in advance depending on the imaging slice position calculation algorithm, and the information is registered in the storage device 112, in association with the imaging site.

The standard imaging slice setter 210 of the present embodiment accepts from the user, reference information as a standard for specifying the standard imaging slice for each imaging site. The reference information is associated with the anatomical feature that is specified in advance with respect to each region, and generated as an imaging slice parameter. The imaging slice parameter being generated is registered in the storage device 112, in association with the imaging site.

In order to implement the configuration above, the standard imaging slice setter 210 of the present embodiment is provided with a reference information acceptor 211 for accepting a setting of the reference information as a standard for specifying the standard imaging slice for each imaging site, and a generator of imaging slice parameter 212 for establishing association between the reference information being accepted and the anatomical feature of the imaging site, being extractable by the anatomical feature extractor 221, and generating the imaging slice parameter.

The reference information acceptor 211 of the present embodiment generates a user interface for accepting the reference information, displays the user interface on the monitor 111, and accepts the reference information via the interface. The user uses the input device 116 to input the reference information. The user interface is generated based on the user interface screen data that is maintained in the storage device 112, in association with the imaging site.

Figure 3:
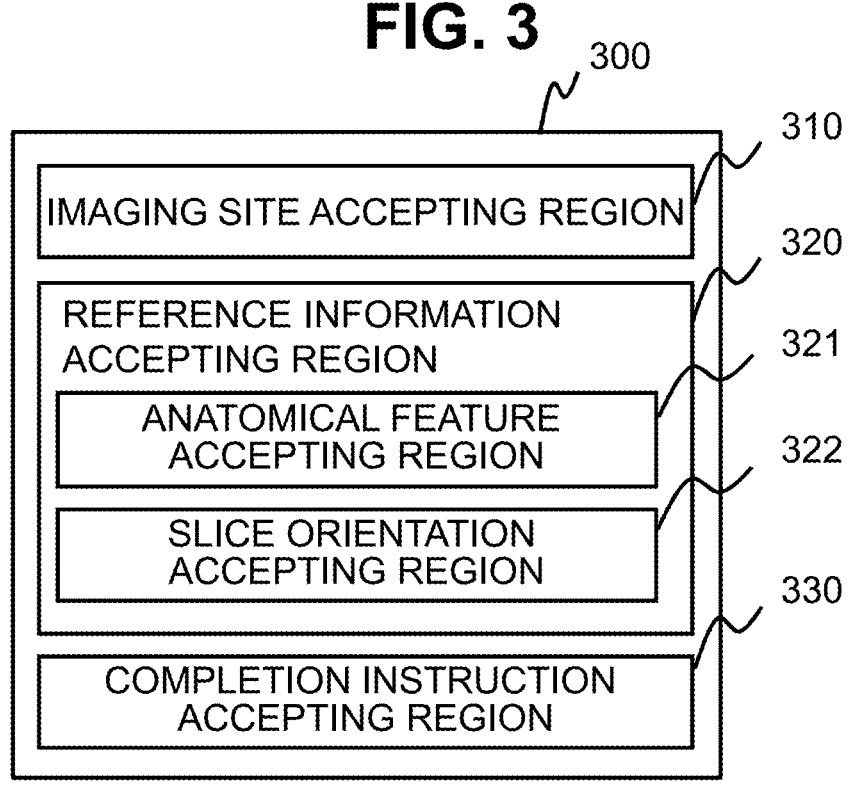
FIG. 3 illustrates an example of a user interface for accepting basic information according to the first embodiment.

FIG. 3 illustrates one example of the user interface 300 for accepting the reference information according to the present embodiment. The user interface 300 of the present embodiment is provided with an imaging site accepting region 310 for accepting an input of the imaging site, a reference information accepting region 320 for accepting the reference information based on the information that is presented depending on the imaging site, and a completion instruction accepting region 330 for accepting an instruction of input completion.

In addition, the imaging slice position in the subject 103 may be uniquely determined by defining the center of the imaging and the inclination of the slice. Therefore, there are accepted as the reference information in the present embodiment, one anatomical feature being information for specifying the center of the imaging range, and a slice orientation for specifying the orientation of the standard imaging slice, being the information for defining the inclination of the slice. In order to accept those information items, the reference information accepting region 320 of the present embodiment is provided with an anatomical feature accepting region 321 and a slice orientation accepting region 322, respectively.

In the present embodiment, the standard imaging slice is specified only by one anatomical feature and the slice orientation. Therefore, in here, any of the axial slice (sagittal plane, coronal plane, or transverse plane) is accepted as the slice orientation.

Upon accepting an instruction of input completion via the completion instruction accepting region 330, the reference information acceptor 211 of the present embodiment accepts the reference information inputted at this timing in the reference information accepting region 320, assuming that it indicates the reference information inputted by the user.

It is to be noted that in the present embodiment, the reference information accepted by the reference information acceptor 211 corresponds to the one anatomical feature and the slice orientation as described above. Therefore, the generator of imaging slice parameter 212 of the present embodiment generates the imaging slice parameter, using thus accepted one anatomical feature and slice orientation being the reference information, without any change.

Figure 4:
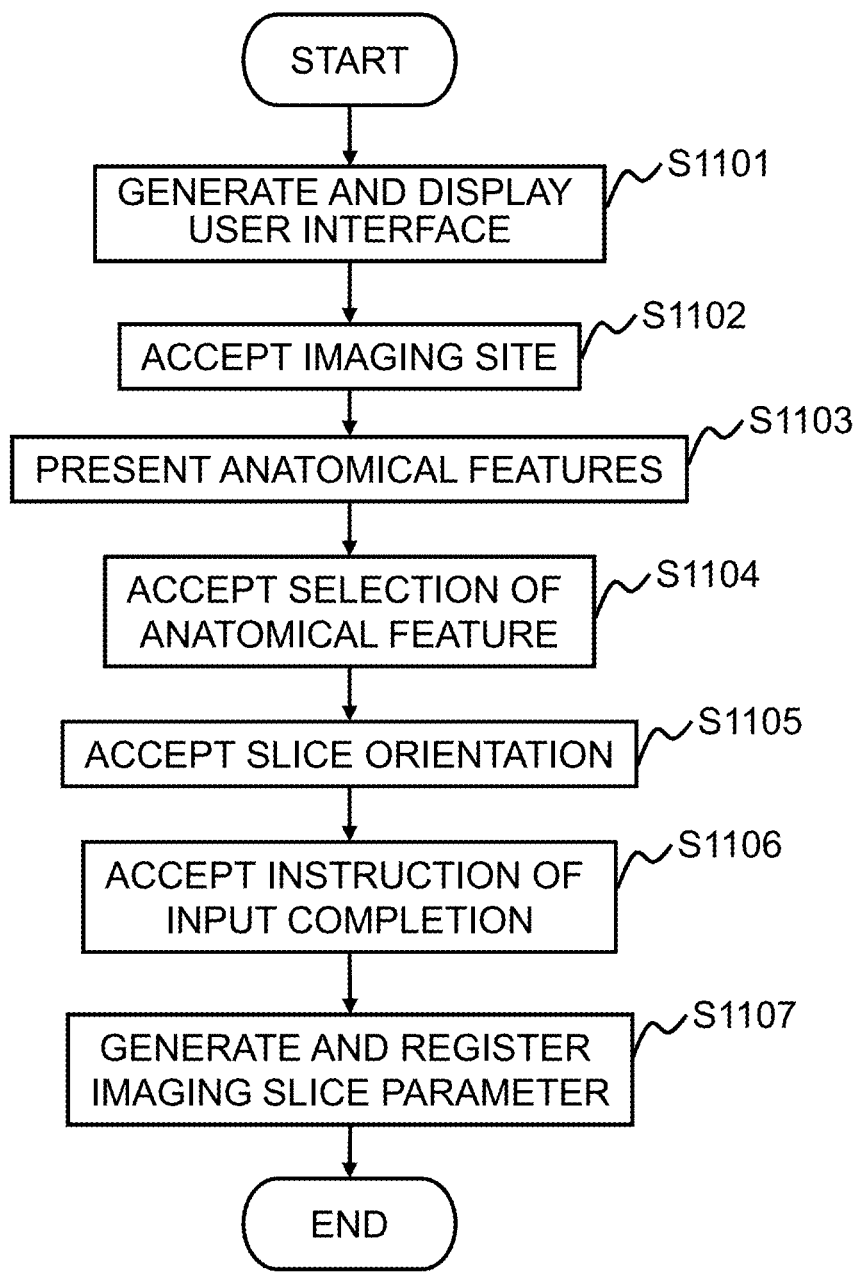
FIG. 4 is a flowchart showing a standard imaging slice setting process according to the first embodiment.

Hereinafter, an explanation will be provided as to a flow of the standard imaging slice setting process according to the standard imaging slice setter 210 of the present embodiment. FIG. 4 is a processing flow of the standard imaging slice setting process according to the present embodiment.

Upon accepting an instruction to start the standard imaging slice setting process, the reference information acceptor 211 generates the user interface 300 and displays the user interface on the monitor 111 (step S1101).

The reference information acceptor 211 accepts an input of the imaging site via the imaging site accepting region 310 (step S1102). Here, information items specifying the imaging target sites (imaging target site names) may be displayed in advance, prompting the user to select an information item, thereby accepting the input of the imaging site. The information items specifying the selectable imaging target sites are registered in advance in the storage device 112.

Next, the reference information acceptor 211 extracts anatomical features (tissue) that are registered in the storage device 112, in association with the selected imaging site, and presents those items in the anatomical feature accepting region 321 in a format being selectable by the user (step S1103). The selectable format is, for example, a menu format, a list format, or the like. By way of example, when the lumbar vertebra is selected as the imaging target site, the centrum, spinal nerves, and interspinal discs are presented to the user.

The user selects an anatomical feature (tissue) from the anatomical features (tissue) being presented, on which the imaging slice is to be set. In this example here, the centrum is selected, for instance. The reference information acceptor 211 accepts an input of the anatomical feature (tissue) via the anatomical feature accepting region 321 (step S1104).

Next, the user sets an orientation of the imaging slice via the slice orientation accepting region 322. The reference information acceptor 211 accepts the orientation of the imaging slice inputted via the slice orientation accepting region 322 (step S1105). According to the procedure as described above, the user inputs reference information necessary for specifying the standard imaging slice.

When the reference information acceptor 211 accepts from the user an instruction of input completion via the completion instruction accepting region 330 (step S1106), the generator of imaging slice parameter 212 generates an imaging slice parameter, using the accepted information specifying the anatomical feature (tissue) (tag; hereinafter, simply referred to as "anatomical feature") and the slice orientation, and registers the imaging slice parameter in the storage device 112 (step S1107).

According to the procedure above, the standard imaging slice setter 210 of the present embodiment accepts from the user the input of the reference information and generates the imaging slice parameter.

Next, an explanation will be provided as to a method for calculating a position (real imaging slice position) of the standard imaging slice being set according to the procedure above, in the imaging target subject 103 to be imaged actually. In the present embodiment, the real imaging slice position calculator 220 performs the calculation, using the imaging slice parameter.

The real imaging slice position calculating process by the real imaging slice position calculator 220 is a process during the examination using the MRI apparatus 100. Prior to explaining the real imaging slice position calculating process by the real imaging slice position calculator 220, an overview of a flow of examination using the MRI apparatus 100 will be explained.

Generally, in the examination using the MRI apparatus 100, scout imaging for acquiring a scout image, preliminary imaging for adjusting the static magnetic field inhomogeneity and correcting coil sensitivity, and main scan for acquiring a diagnostic image of the imaging slice being determined, are executed sequentially. The real imaging slice position calculating process of the present embodiment is executed after the scout imaging before performing the main scan.

Each imaging is made up of at least one measurement, and each measurement is performed according to a pulse sequence and imaging parameters. The order of imaging in each examination, the order of measurement, and a type of measurement in each imaging are defined by a protocol. The protocol is generated, for instance, depending the an examination target region (imaging site) such as regions of head, lumbar vertebra, knee, and shoulder, and intended disease, and the protocol includes the pulse sequence executed in each imaging and imaging parameters thereof. The user generates the protocol prior to executing the examination, and it is stored in the storage device 112. The examination using the MRI apparatus 100 is executed according to the protocol that is generated depending on the imaging site.

The pulse sequence used in each imaging, the imaging parameters inputted from the user, and the like, are registered in the storage device 112. The registered pulse sequence may be, for instance, FSE (Fast Spin Echo), GrE (Gradient Echo), EPI (Echo Planar Imaging), or the like, and the imaging parameter may be, TR (repetition time), TE (echo time), FOV (imaging field of view), slice thickness, the number of slices, the order of imaging in the case of imaging multiple slices, or the like.

It is also possible to configure such that the user generates the protocol for each examination via the user interface, and it is registered in the storage device 112. Alternatively, the protocol may be generated in advance for each examination region and/or disease, and stored in the storage device 112. In the case where it is stored in advance, the user extracts one for each examination from the protocols being stored, and decides the protocol to be used. It is further possible to configure such that an optimum protocol is stored in association with each examination region (imaging site) in the storage device 112, and when the user designates the examination region (imaging site) upon setting the imaging parameter, a protocol being in association with this designated examination region (imaging site) is extracted as an initial value of the optimum protocol.

In the present embodiment, the protocol being registered further includes information relating to the real imaging slice position calculating process, such as whether or not the real imaging slice position calculating process is executed, and an imaging slice position calculation algorithm to be used in executing the process. When the real imaging slice position calculating process is executed, optimum scout imaging information is registered, defining the procedure of the scout imaging that is optimum for the real imaging slice position calculation. Specifically, there are registered the pulse sequence used in the scout imaging, the imaging parameters, the slice to be imaged, and the order of imaging, if multiple slices are imaged. The setting for executing the real imaging slice position calculating process may be configured in such a manner that the setting synchronizes with the selection and setting of the optimum scout imaging, upon generating the protocol. It is further possible configure such that a parameter for deciding whether or not the real imaging slice position calculating process is executed is added to the imaging parameters for the main scan, and when it is selected to execute this process, the optimum scout imaging is registered in the protocol.

It is to be noted that the storage device 112 registers the imaging slice position calculation algorithm in association with each imaging site, and a condition of the optimum scout imaging according to the real imaging slice position calculating process for each imaging site.

Figure 5:
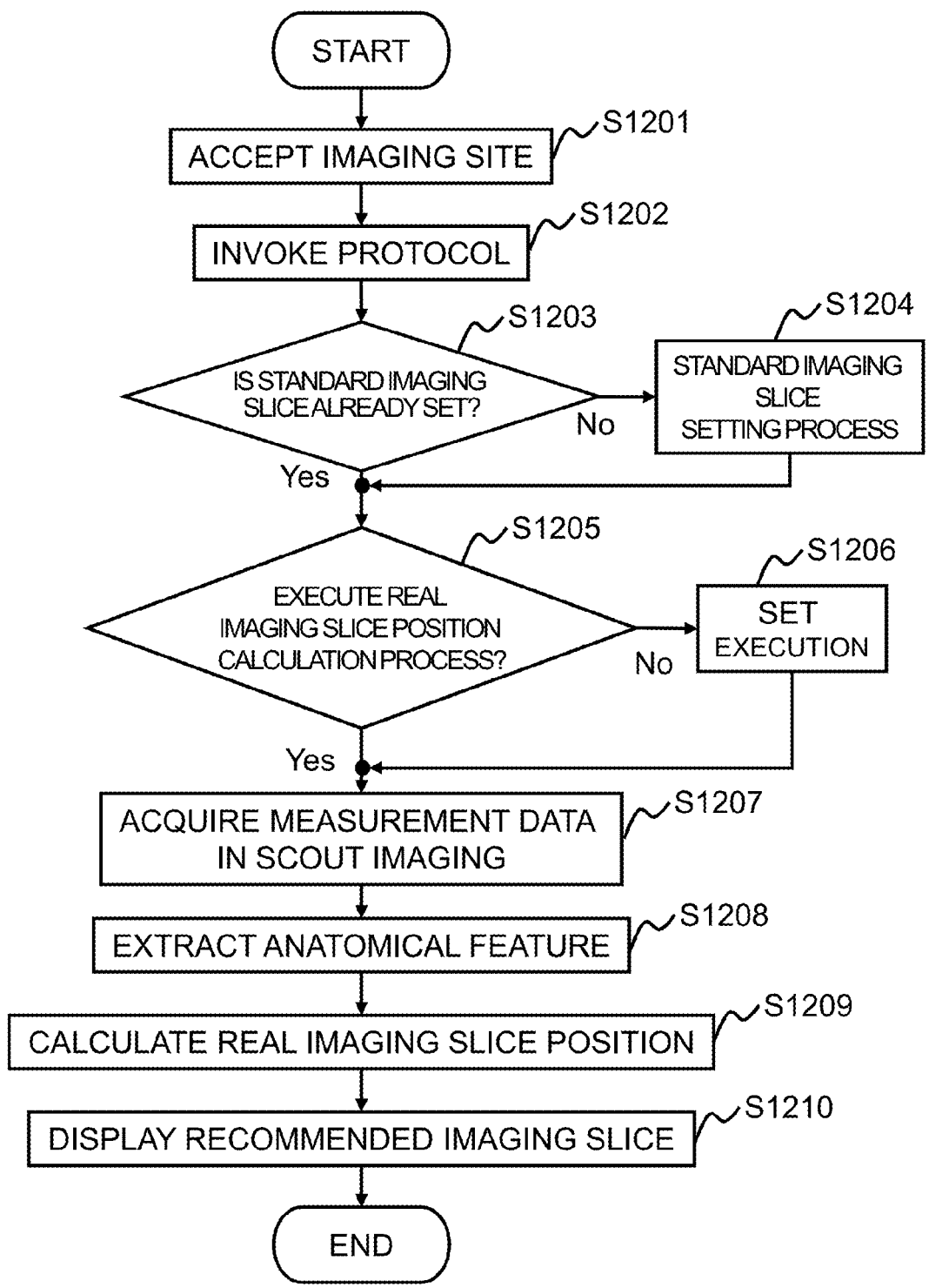
FIG. 5 is a flowchart showing a process from starting examination to the end of the real imaging slice position calculating process according to the first embodiment.

Next, there will be explained a flow of the examination in the present embodiment until the end of the real imaging slice position calculating process according to the real imaging slice position calculator 220. FIG. 5 is a flow of the examination in the present embodiment. Here, a routine examination of the spine will be explained, by way of example.

Firstly, the computer 110 accepts from the user, a designation of the examination region (imaging site) (step S1201). By way of example, the imaging site is accepted, designating the lumbar vertebra.

The computer 110 invokes the protocol registered in the storage device 112, in association with the examination region (imaging site) being designated (step S1202). In this example here, since it is designated as the lumbar vertebra, the protocol for examining the lumbar vertebra is invoked.

Then, the computer 110 determines whether or not a standard imaging slice is set in association with the examination region (imaging site) being designated (step S1203). In the case of examining the lumbar vertebra, it is determined whether or not setting of the standard imaging slice relating to the lumbar vertebra examination is completed. As discussed above, in the present embodiment, when the standard imaging slice for each imaging site is set, the standard imaging slice setter 210 generates the imaging slice parameter that is calculated from the reference information, and registers the parameter in the storage device 112 in association with the imaging site. Therefore, in this example here, the computer 110 determines whether or not the imaging slice parameter is registered in the storage device 112, in association with the imaging site. If it is registered, the process proceeds to the next step. If it has not been registered yet, the standard imaging slice setter 210 is made to perform the standard imaging slice setting process with regard to the imaging site (step S1204).

Next, the computer 110 determines whether or not the protocol being invoked is configured as executing the real imaging slice position calculating process (step S1205). If it is configured as executing the process, the process proceeds to the next step. If it has not been configured yet, the settings of the protocol are changed to execute the process (step S1206).

Next, the computer 110 executes scout imaging according to the settings of the protocol, and acquires measurement data (scout data) of the imaging target subject 103 (step S1207).

Next, the anatomical feature extractor 221 uses the imaging slice position calculation algorithm registered in the protocol that is extracted in the step S1202, and extracts the anatomical feature of the imaging target subject 103 from the measurement data (scout image) that is acquired in the step S1207 (step S1208). In this example here, according to a general image processing method, such as a pattern matching process and an edge extraction process, a tissue form, spacial position, the coordinate of the center of gravity, and the like, of the imaging site are extracted as the anatomical feature. By way of example, in the case of routine examination of the spine, the spacial position, the shape, and the coordinate of the center of gravity, and the like, of the centrum, interspinal discs, and spinal nerves, are calculated.

Next, the real imaging slice position calculator 220 uses the imaging slice parameter based on thus extracted anatomical feature (tissue), to calculate the real imaging slice position (step S1209). In the present embodiment, the anatomical feature (tissue) at the center of the imaging slice and the orientation of the slice are registered as the imaging slice parameter. Therefore, on the imaging target subject 103, a slice whose center is equivalent to the center of gravity coordinates of the anatomical feature (tissue) being designated as the imaging slice parameter, and whose orientation corresponds to the slice orientation designated by the imaging slice parameter, is determined as the real imaging slice position. By way of example, in the case where the centrum and the sagittal plane are registered as the imaging slice parameters, the real imaging slice position calculator calculates an imaging slice the center of which corresponds to the center of gravity coordinate of the centrum, and its orientation indicates the orientation of the sagittal plane.

Then, the display part 230 displays the real imaging slice position calculated by the real imaging slice position calculator 220, as a recommended imaging slice position, on a position locating image (scout image) displayed on the monitor 111 (step S1210).

According to the processing as described above, the recommended imaging slice position is presented to the user. The user checks the recommended imaging slice position being presented and execute the real imaging at the position as it is, if appropriate, or executes the main scan after adjustment, if necessary.

It is to be noted that in the processing above, as for the standard imaging slice setting process of the step S1204, it is sufficient if it is executed only once for each target region. On the other hand, the real imaging slice position calculating process in the step S1209 is performed for each imaging site in every examination.

As discussed above, the medical imaging apparatus of the present embodiment is an apparatus such as an MRI apparatus 100, which is capable of setting any plane in three-dimensional space as an imaging slice, and it is provided with, a standard imaging slice setter 210 for setting an imaging slice being recommended depending on the imaging site as the standard imaging slice, and generating an imaging slice parameter from the standard imaging slice being set, a real imaging slice position calculator 220 for calculating a real imaging slice position as a position of the standard imaging slice in the imaging target subject 103, and a display part 230 for displaying the real imaging slice position for the user as the recommended imaging slice, and the real imaging slice position calculator 220 is provided with the anatomical feature extractor 221 for extracting the anatomical feature on the scout image, of the imaging target subject 103, and calculates the real imaging slice position by using the imaging slice parameter and the anatomical feature, the standard imaging slice setter 210 is provided with the reference information acceptor 211 for accepting a setting of reference information as a reference for specifying the standard imaging slice, and a generator of imaging slice parameter 212 for establishing association between the reference information and the anatomical feature that is extractable by the anatomical feature extractor 221 to generate the imaging slice parameter.

As thus described, according to the present embodiment, information defining the standard imaging slice is inputted via the reference information acceptor 211, thereby setting the standard imaging slice. Therefore, the user is allowed to configure the imaging slice being automatically set, according to the user's preferences. In addition, the reference information for specifying the standard imaging slice for each imaging site, the standard imaging slice being set by the user on a standard image, is registered in association with the anatomical feature of the imaging site. Then, upon performing the real imaging, a position of the standard imaging slice on the imaging target subject 103 is specified, based on the anatomical feature of the imaging target subject 103. Therefore, it is possible to decide automatically with a high degree of accuracy, a position of the standard imaging slice being set on the imaging target subject 103.

In other words, it is not necessary for the user to adjust the position of the imaging slice every time a new subject is imaged. Accordingly, setting of the imaging slice of a target region is performed only when it is necessary, and therefore, the load for the setting may be mitigated.

The reference information acceptor 211 is provided with an imaging site acceptor (the imaging site accepting region 310) for accepting an input of an imaging site, and inputting of the reference information may be accepted based on the information that is presented according to the imaging site being accepted in the imaging site acceptor. Then, the reference information acceptor 211 accepts designation of one anatomical feature, as the information for specifying the center of the standard imaging slice in the reference information. The generator of imaging slice parameter 212 may assume the anatomical feature accepted by the reference information acceptor 211 as the imaging slice parameter. The reference information acceptor 211 accepts a designation of the slice orientation as the information for specifying the inclination of the standard imaging slice in the reference information, and the generator of imaging slice parameter 212 may assume the slice orientation accepted by the reference information acceptor 211 as the imaging slice parameter.

Therefore, the user is allowed to configure easily the imaging slice being automatically set, according to the user's preferences.

In the embodiment as described above, it is configured such that an axial slice, like the transverse plane, coronal plane, and sagittal plane, is designated as the information defining the inclination of the standard imaging slice, but the axial slice is not the only example. Any information may be applicable, if it is possible to identify the standard imaging slice.

By way of example, it is further possible to configure such that orientation of the imaging plane is selectable, being the most recommendable for the anatomical feature (tissue) that is selected via the anatomical feature accepting region 321. On this occasion, optimum imaging planes (optimum orientation planes) are registered in the storage device 112, those planes respectively being associated with the extractable tissue, in advance.

By way of example, in the case of the centrum, the optimum orientation plane is a plane being parallel to the spinal nerves and passing through the center of the centrum. In the case of the interspinal disc, the optimum orientation plane is a plane being parallel to the inclination of the interspinal disc. Those optimum orientation planes above are set based on the anatomical feature that is extracted according to the imaging slice position calculation algorithm.

Accordingly, the user is allowed to set an optimum imaging slice, even though he or she is unaccustomed to the examination.

It is further possible to configure such that according to the designation of the imaging site, an optimum slice orientation as an initial value is displayed and inputted in the slice orientation accepting region 322. With the configuration as described above, inputting only the anatomical feature allows completion of inputting the reference information. Therefore, inputting by the user in the standard imaging slice setting process is simplified, and thereby enhancing the operability.

Furthermore, in the present embodiment, the anatomical feature (tissue) and the slice orientation are used as the reference information for defining the standard imaging slice, but those are not the only example. By way of example, it is also possible to configure such that multiple anatomical features capable of specifying one slice are inputted as the reference information. On this occasion, the anatomical features being inputted are assumed as the imaging slice parameters.

It is further possible to configure such that anatomical features for defining the imaging center and the orientation of the standard imaging slice are designated as basic information. By way of example, the anatomical feature defining the imaging center is selected from the coordinates of extractable anatomical features, and then designated. As the anatomical feature for defining the orientation, coordinate points, vectors, and planes are combined, defined by the device coordinate system determined by the magnetic field direction and the extractable anatomical features, and thereby designating anatomical feature that is able to decide the first vector and the second vector on the imaging plane. The anatomical features respectively designated above, together with the first vector and the second vector are assumed as the imaging slice parameters.

Here, an example will be explained for selecting an orthogonal tissue being orthogonal to the standard imaging slice and a parallel tissue being parallel thereto, as the first vector and the second vector of the reference information, respectively, taking the lumbar vertebra examination as an example.

By way of example, when an imaging slice of the centrum is set in the lumbar vertebra examination, the center of the third lumbar vertebra is selected as the imaging center, and as the orientation, the spinal nerves direction on a coronal image (the first vector), and the direction of a line connecting the center of the centrum and the spinal nerves on the axial image (the second vector) are selected.

When an imaging slice of the interspinal disc is set in the lumbar vertebra examination, the center of the interspinal disc between the second lumbar vertebra and the third lumbar vertebra as the imaging center, and as the orientation, the inclination of the interspinal disc between the second lumbar vertebra and third lumbar vertebra on the coronal image (the first vector), and the inclination of the interspinal disc between the second lumbar vertebra and third lumbar vertebra on the sagittal image (the second vector) are selected.

In the head region examination, if an imaging slice along the ON line is set, the center of the brain is selected as the imaging center, and as the orientation, the direction vertical to the midsagittal plane (the first vector) and the direction of OM line direction (the second vector) on the midsagittal plane are set. On this occasion, the coordinates of the nasal root and the bridge lower portion on the midsagittal plane image may be selected, and the orientation connecting those coordinates may be set as the second vector.

When an imaging slice is set in the liver examination, the center of the liver is selected as the imaging center, and as the orientation, the x-axis (the first vector) and the y-axis (the second vector) of the device coordinate are set. Here, in the device coordinate system, the z-axis is assumed as the magnetic field direction, the x-axis is assumed as the horizontal direction, and the y-axis is assumed as the vertical direction, for instance.

It is to be noted that if it is configured such that an input of multiple tissues is accepted on which the slice is identifiable, the slice orientation accepting region 322 becomes unnecessary in the user interface 300.

In the present embodiment, the anatomical feature is inputted as the information for specifying the center in the reference information, but this is not the only example. As a simpler designation method, it is further possible to configure in such a manner that a name of the tissue is designated, the tissue including a particular anatomical feature. With this configuration, the user is allowed to set the standard imaging slice intuitively and easily. In this case, the tissue capable of being designated is held in the storage device 112, in association with the imaging site in advance.

In addition, the user interface 300 may be configured as being provided with a position-locating image displaying region. On this occasion, when the imaging site is inputted (selected) via the imaging site accepting region 310, a standard image being a typical slice image of the inputted (selected) imaging site is displayed in the position-locating image displaying region. It is further possible to display in an identifiable manner on the standard image, the anatomical feature of the selected imaging site, the anatomical feature being extractable by the imaging slice position calculation algorithm. The identifiable display may be implemented by a method such as changing the color from other display, for instance.

In addition, when the user interface 300 is provided with the position-locating image displaying region, it is also possible to configure such that the anatomical feature being inputted as the reference information is able to be inputted via this position-locating image displaying region. By way of example, the user clicks by the mouse, a tissue on the standard image, and this allows inputting, selecting, and accepting the anatomical feature.

Similarly, it is possible to configure such that the orientation (any of the axial slices) inputted in the slice orientation accepting region 322 is displayed on the standard image.

The user interface 300 is provided with the position-locating image displaying region, and the reference information acceptor 211 displays the standard image of the imaging site accepted by the imaging site accepting region 310, and accepts an input via the standard image, and such configuration as described above allows the user to perform visual operation. Therefore, this enhances the operability.

It is further possible to configure such that multiple standard imaging slices may be set for any imaging site. In this case, the imaging slice parameters obtained from the reference information that specifies each standard imaging slice are registered in the storage device 112, in such a form that makes each parameter identifiable. As the form for making the parameters identifiable, each imaging slice parameter is labeled with a name or the like, for instance. Then, the name is registered in the protocol, thereby specifying the imaging slice parameter to be used. With the configuration as described above, it is possible to manage the case where imaging at multiple imaging positions is necessary in the main scan.

In the embodiment as described above, the reference information acceptor 211 accepts the information directly including the anatomical feature as the reference information, but this is not the only example.

By way of example, it is further possible to configure such that an optional one point (central reference point) is accepted as the information for specifying the center of the standard imaging slice, and optional two points (inclination reference points) are accepted as the information for specifying the inclination, as the reference information. The standard image of the imaging site is displayed as the user interface, so as to accept those information items above on the standard image.

Hereinafter, an explanation will be provided as to the user interface generated by the reference information acceptor 211, and a procedure of the standard imaging slice setting process, in the case where the inclination and the center of the imaging slice are inputted as the reference information. In here, by way of example, the case of the routine examination of the head region will be explained where the imaging slice is set assuming the midsagittal plane as a reference. In this example here, a vector being vertical to the midsagittal plane is designated as the first vector, and the user designates the imaging center and the second vector, as the center and the inclination of the standard imaging slice, respectively.

Figure 6:
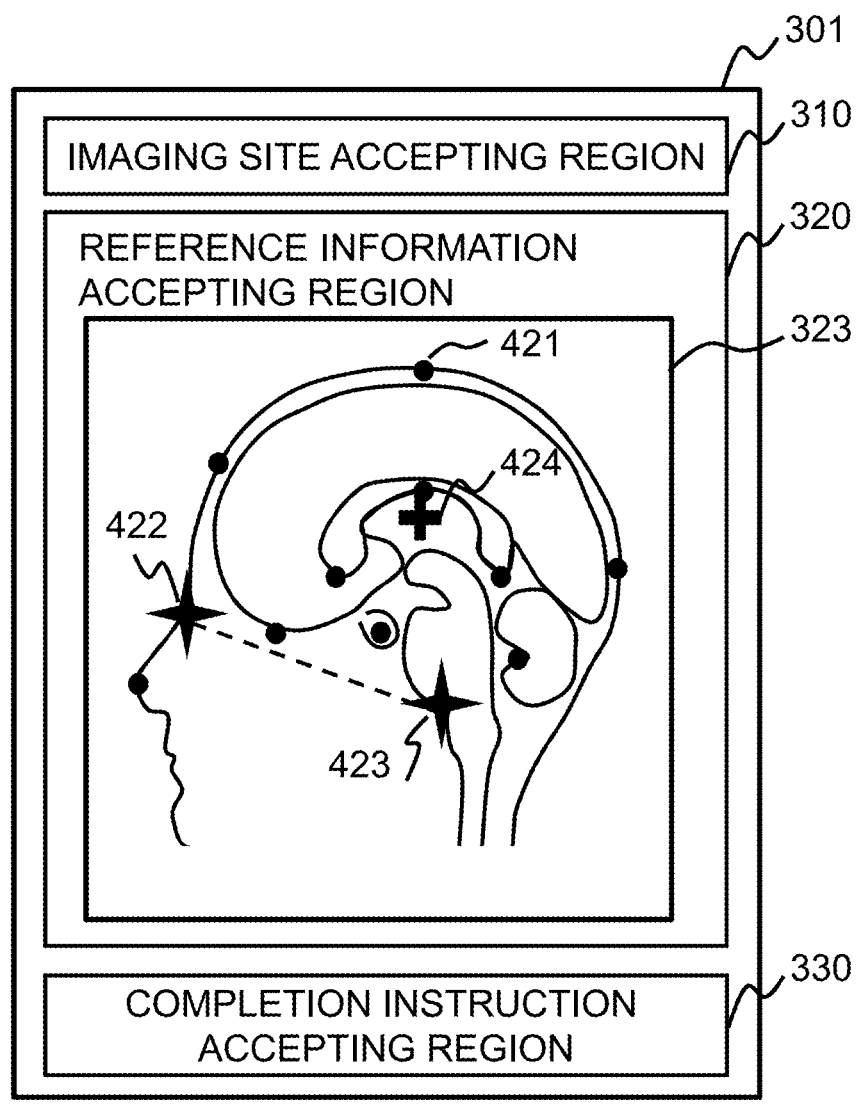
FIG. 6 illustrates another example of the user interface for accepting the basic information according to the first embodiment.
Figure 7:
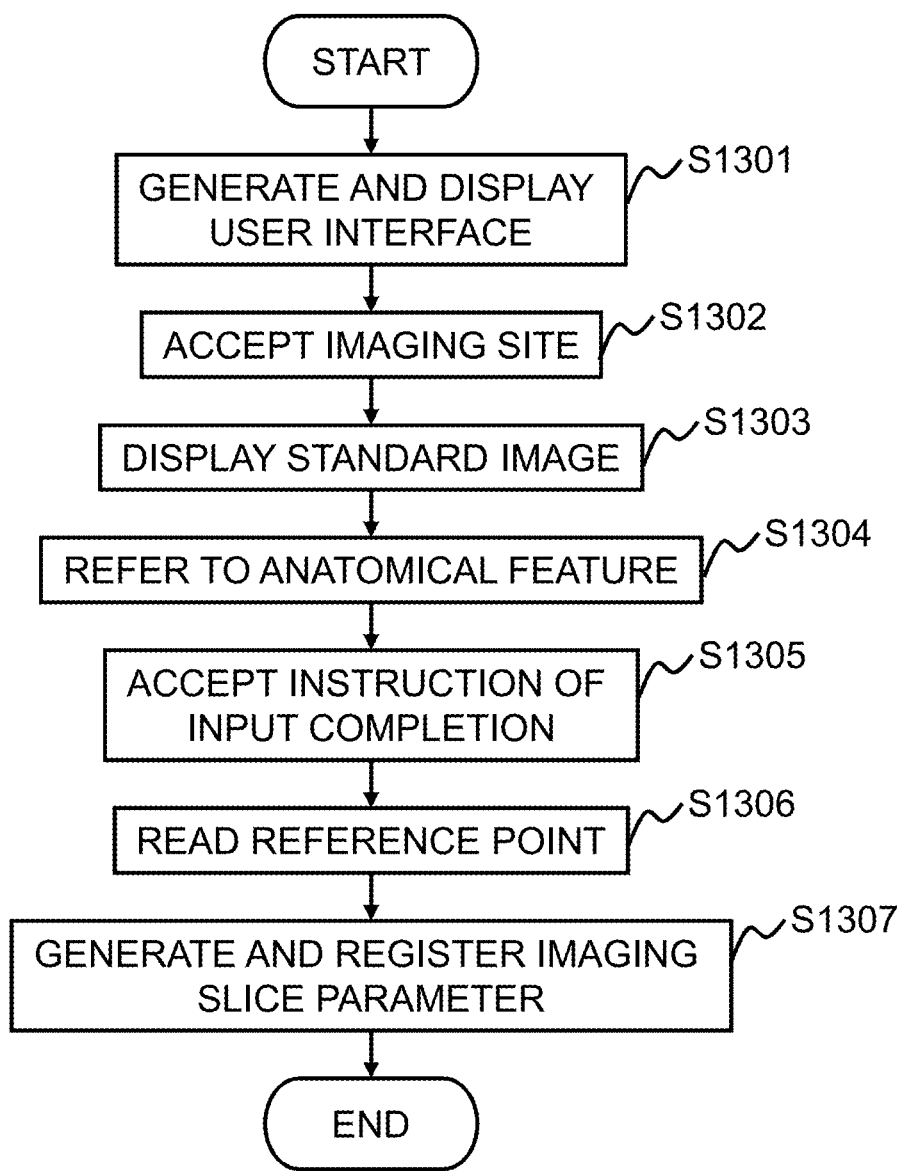
FIG. 7 is a flowchart showing another example of the standard imaging slice setting process according to the first embodiment.

FIG. 6 illustrates one example of the user interface 301 that is generated by the reference information acceptor 211 according to the modification example. FIG. 7 is a processing flow showing a flow of the standard imaging slice setting process according to the standard imaging slice setter 210.

As illustrated, the user interface 301 is provided with an imaging site accepting region 310, a reference information accepting region 320, and a completion instruction accepting region 330. The imaging site accepting region 310 and the completion instruction accepting region 330 are configured the same as those with the same names in the aforementioned embodiment. Meanwhile, the reference information accepting region 320 of the modification example accepts reference information for specifying the standard imaging slice, similar to the aforementioned embodiment. In the present embodiment, the reference information accepting region 320 is provided with an image displaying region 323 for accepting the reference information on the image.

The image displaying region 323 is a region for displaying the standard image (slice image) of the imaging target site accepted from the user via the imaging site accepting region 310, and accepting an input of the reference information from the user. The standard image is the position-locating image being selectable according to the imaging site, and it is registered in advance in the storage device 112 for each imaging target site.

The reference information acceptor 211 accepts inputting of the reference information via the image displaying region 323. Here, the inclination and the center of the standard imaging slice are accepted. In order to specify the inclination of the standard imaging slice, the user designates two points (inclination reference points 422 and 423) that specify the inclination. In addition, in order to specify the center, one point (central reference point 424) is also designated. The user is allowed to freely decide (input) the positions of the reference points within the image displaying region 323.

It is possible to configure such that the anatomical feature 421 being extractable by the imaging slice position calculation algorithm of the imaging site being inputted is simultaneously displayed in the image displaying region 323. Here, the anatomical feature 421 may be hidden.

Upon accepting an instruction of input completion via the completion instruction accepting region 330, the generator of imaging slice parameter 212 of the modification example calculates the imaging slice parameter, based on the inclination and the center being inputted in the image displaying region 323 at that point of time.

Hereinafter, a flow of the standard imaging slice setting process according to the standard imaging slice setter 210 of the present modification example will be explained along the flow of FIG. 7.

Upon accepting an instruction to start the standard imaging slice setting process, the reference information acceptor 211 generates the user interface 301 and displays the user interface on the monitor 111 (step S1301).

The reference information acceptor 211 accepts an input of the imaging site via the imaging site accepting region 310 (step S1302). In here, information items (site names) specifying regions being selectable are displayed in advance, prompting the user to select any of them, thereby accepting the input of the imaging site. The information items specifying the selectable regions are registered in advance in the storage device 112.

Next, the reference information acceptor 211 extracts the standard image being registered in the storage device 112, in association with the selected imaging site, and displays the standard image in the image displaying region 323 (step S1303). If the imaging site corresponds to the brain, a midsagittal plane image is displayed, for instance. On this occasion, it is further possible to configure such that initial values of the inclination reference points 422 and 423, and an initial value of the central reference point 424 are displayed together. If the initial values are displayed, those values are registered in advance in the storage device 112. In addition, the reference information acceptor 211 refers to the anatomical feature being extractable by the imaging slice position calculation algorithm, being registered in the storage device 112, in association with the inputted imaging site (step S1304). On this occasion, the anatomical feature being referred to may be displayed on the standard image in the image displaying region 323. It is further possible to configure such that the imaging slice position calculation algorithm is executed for the standard image, to extract the anatomical feature that is extractable by the imaging slice position calculation algorithm.

Here, the user inputs initial values of two inclination reference points 422 and 423 and an initial value of one central reference point 424, as the reference information on the standard image displayed in the image displaying region 323, and thereafter freely adjusts the positions of the inclination reference points 422 and 423 and the central reference point 424, to desired positions. It is to be noted that if the initial values are displayed, only the adjustment is performed. Then, upon completing the adjustment to the desired positions, a decision of input completion is inputted via the completion instruction accepting region 330.

When the reference information acceptor 211 accepts the instruction indicating the input completion from the user, via the completion instruction accepting region 330 (step S1305), the generator of imaging slice parameter 212 reads the inclination reference points 422 and 423 and the central reference point 424, being set on the standard image at that point of time (step S1306), calculates the imaging slice parameter, and registers the parameter in the storage device 112 (step S1307).

Here, an explanation will be made as to the imaging slice parameter generating process for calculating the imaging slice parameter according to the generator of imaging slice parameter 212, based on the inclination reference points 422 and 423 and the central reference point 424 in the step S1307.

The imaging slice parameter generating process of the modification example obtains calculation information for calculating the inclination reference points 422 and 423, and the central reference point 424, respectively, from the predetermined anatomical feature. Then, the anatomical feature and the calculation information being obtained are set as the imaging slice parameters.

Firstly, an explanation will be provided as to the imaging slice parameter being calculated from the inclination reference points 422 and 423, and a method for the calculation. The generator of imaging slice parameter 212 extracts the anatomical features (proximity feature points) in proximity (or the closest) to the inclination reference points 422 and 423, respectively, out of the anatomical features being extractable by the imaging slice position calculation algorithm. Then, difference values between the proximity feature points and the inclination reference points 422 and 423, respectively, are calculated. Thus obtained difference values are standardized by the distance between the two proximity feature points, and the standardized difference values are obtained as the calculation information.

The processing above will be explained, using a specific example. Here, the coordinates of the inclination reference points 422 and 423 designated by the user are assumed as (x1, y1) and (x2, y2), respectively. The coordinates of the proximity feature points are assumed as (nx1, ny1), and (nx2, ny2), respectively, and the distance between the two proximity feature points is assumed as NL. The standardized difference values (dx1, dy1) and (dx2, dy2) are calculated according to the following formula (1):

$$\begin{pmatrix} dx1 \\ dy1 \end{pmatrix} = \begin{pmatrix} \frac{(nx2-nx1)\cdot(x1-nx1)+(ny2-ny1)\cdot(y1-ny1)}{NL^2} \\ \frac{-(ny2-ny1)\cdot(x1-nx1)+(nx2-nx1)\cdot(y1-ny1)}{NL^2} \end{pmatrix}$$

$$\begin{pmatrix} dx2 \\ dy2 \end{pmatrix} = \begin{pmatrix} \frac{(nx2-nx1)\cdot(x2-nx1)+(ny2-ny1)\cdot(y2-ny1)}{NL^2} \\ \frac{-(ny2-ny1)\cdot(x2-nx1)+(nx2-nx1)\cdot(y2-ny1)}{NL^2} \end{pmatrix} \quad (1)$$

The generator of imaging slice parameter 212 stores the standardized difference values and information for specifying the proximity feature points, as the imaging slice parameters.

It is to be noted that real imaging slice position calculator 220 uses the standardized difference values (dx1, dy1) and (dx2, dy2), and the information specifying the proximity feature points, so as to obtain the inclination reference points 422 and 423 of the subject, from the coordinates of the proximity feature points of an arbitrary subject.

In other words, when the coordinates of the proximity feature points of the predetermined subject, being extracted according to the imaging slice position calculation algorithm are assumed as (nx1', ny1') and (nx2', ny2'), and the distance between the two proximity feature points is assumed as NL', the inclination reference points (x1', y1') and (x2', y2') of the subject are provided by the following formula (2), respectively:

$$\begin{pmatrix} x1' \\ y1' \end{pmatrix} = \begin{pmatrix} nx1' \\ ny1' \end{pmatrix} + dx1 \cdot \begin{pmatrix} nx2'-nx1' \\ ny2'-ny1' \end{pmatrix} + dy1 \cdot \begin{pmatrix} -(ny2'-ny1') \\ nx2'-nx1' \end{pmatrix}$$

$$\begin{pmatrix} x2' \\ y2' \end{pmatrix} = \begin{pmatrix} nx2' \\ ny2' \end{pmatrix} + dx2 \cdot \begin{pmatrix} nx2'-nx1' \\ ny2'-ny1' \end{pmatrix} + dy2 \cdot \begin{pmatrix} -(ny2'-ny1') \\ nx2'-nx1' \end{pmatrix} \quad (2)$$

Here, it is assumed that the imaging field of view (FOV) of the image of the arbitrary subject to be analyzed is equivalent to the FOV of the slice image being displayed in the image displaying region 323.

Next, an explanation will be provided as to the imaging slice parameter calculated from the central reference point 424, and a calculation method thereof. It is to be noted here that multiple anatomical features (reference feature points) are decided in advance, to be used in calculating the imaging slice parameter, among the anatomical features extractable by the algorithm. The number of the reference feature points is assumed as at least three. The generator of imaging slice parameter 212 calculates a weight (shape function) for obtaining the coordinates of the central reference point 424 from all the reference feature points. This shape function is assumed as the calculation information. It is to be noted that the real imaging slice position calculator 220 uses the associated reference feature points and the shape function of the arbitrary subject, so as to calculate the central reference point 424 of the subject by interpolation. The reference feature points to be used are set in the form of initial values, and held in the storage device 112. Alternatively, those may be designated by the user.

The processing above will be explained, using a specific example. Here, an explanation will be provided, taking as an example the case that four points are employed as the reference feature points. The coordinates of the central reference point 424 are assumed as (x0, y0), and the coordinates of the reference feature points are assumed as (nx1, ny1), (nx2, ny2), (nx3, ny3), and (nx4, ny4), respectively. The shape functions $N_1$, $N_2$, $N_3$, and $N_4$ are defined as the following formula (3) by using the constants s and t.

$$\begin{aligned} N_1 &= \frac{1}{4}(1-s)(1-t) \\ N_2 &= \frac{1}{4}(1+s)(1-t) \\ N_3 &= \frac{1}{4}(1+s)(1+t) \\ N_4 &= \frac{1}{4}(1-s)(1+t) \end{aligned} \quad (3)$$

According to the following simultaneous equation (4), the generator of imaging slice parameter 212 obtains the constants (s, t), and calculates values of the shape functions $N_1$, $N_2$, $N_3$, and $N_4$, respectively.

$$x0 = N_1 \cdot nx1 + N_2 \cdot nx2 + N_3 \cdot nx3 + N_4 \cdot nx4 \brace y0 = N_1 \cdot ny1 + N_2 \cdot ny2 + N_3 \cdot ny3 + N_4 \cdot ny4 \quad (4)$$

The generator of imaging slice parameter 212 stores the aforementioned shape functions and the information for specifying the reference feature points, as the imaging slice parameters.

It is to be noted that by using the shape functions $N_1$, $N_2$, $N_3$, and $N_4$ as obtained above, the real imaging slice position calculator 220 is allowed to obtain the central reference point 424 of the arbitrary subject, according to the coordinates of the associated reference feature points in the subject.

When the coordinates of the associated reference feature points of the predetermined subject, being extracted according to the imaging slice position calculation algorithm, are assumed as (nx1', ny1'), (nx2', ny2'), (nx3', ny3'), and (nx4', ny4'), the coordinates of the central reference point 424 (x0', y0') of the subject may be calculated according to the following formula (5).

$$x0' = N_1 \cdot nx1' + N_2 \cdot nx2' + N_3 \cdot nx3' + N_4 \cdot nx4' \brace y0' = N_1 \cdot ny1' + N_2 \cdot ny2' + N_3 \cdot ny3' + N_4 \cdot ny4' \quad (5)$$

As discussed above, by generating the imaging slice parameters, the real imaging slice position calculator 220 is able to calculate points on the predetermined subject, respectively corresponding to the inclination reference points 422 and 423, and the central reference point 424. The real imaging slice position calculator 220 uses the calculated central reference point 424 and the inclination reference points 422 and 423 to specify the real imaging slice position.

As described above, according to the present modification example, the reference information acceptor 211 accepts a specific one point as the reference point on the standard image, as the information for specifying the center of the standard imaging slice in the reference information, and the generator of imaging slice parameter 212 may assume the predetermined anatomical feature and calculation information for calculating the reference point from the anatomical feature, as the imaging slice parameters. On this occasion, the calculation information may be assumed as the shape function. The reference information acceptor 211 accepts particular two points on the standard image being the reference points, as the information specifying the inclination of the standard imaging slice in the reference information, and the generator of imaging slice parameter 212 may assume the anatomical features respectively in proximity to the reference points and the calculation information for calculating the reference points from the respective anatomical features, as the imaging slice parameters. On this occasion, the calculation information may be standardized difference values, from the proximity anatomical features of the respective reference points.

In other words, according to the present modification example, a combination of the standardized difference value and the proximity feature point, and a combination of the shape function and the reference feature point are generated as the imaging slice parameters. Upon calculating the real imaging slice position of the arbitrary subject, the real imaging slice position calculator 220 refers to those imaging slice parameters, and calculates the inclination and the center point of the real imaging slice of the subject.

With this configuration, the user is allowed to set a desired standard imaging slice with a higher flexibility. In addition, it is possible to perform positioning of the standard imaging slice set by the user, on the imaging target subject, automatically with a high degree of accuracy.

In addition, in the example where the center and the inclination of an optional position are inputted as the reference information, a method for generating the imaging slice parameters according to the generator of imaging slice parameter 212, and the calculation information of thus generated imaging slice parameters are not limited to those described above. By way of example, they may be organizational structure patterns, around the central reference point and the inclination reference points.

Hereinafter, an explanation will be provided as to a configuration assuming the inclination reference points 422 and 423 as examples, in which pixel density patterns are extracted as the calculation information, in micro regions around the inclination reference points 422 and 423, establishing association between the pixel density patterns and the proximity feature points, and then, they are registered as the imaging slice parameters.

On this occasion, firstly, in the standard image (slice image) displayed in the image displaying region 323, images of the micro regions are generated, centering the inclination reference points 422 and 423, respectively. The region of thus generated image is set in advance as an micro-image field of view (FOV) depending on the standard image (slice image) being displayed. By way of example, the region is set to be 20 mm×20 mm, as the micro-image FOV in the midsagittal plane image.

The coordinates of the inclination reference points 422 and 423 are respectively assumed as (x1, y1) and (x2, y2), and the coordinates of the closest feature points (proximity feature points) being extracted are respectively assumed as (nx1, ny1) and (nx2, ny2). Each of the inclination reference points 422 and 423, and the proximity feature points thereof respectively, are extracted, and the distance NL1 and NL2 between the inclination reference points 422 and 423 and the respective proximity points, and the distance NL between each of the proximity feature points are calculated. Then, the generated micro-region images, the information specifying each proximity feature point (tag), the distance between each inclination reference point and the proximity feature point thereof, and the distance between the proximity feature points are registered in the storage device 122, as the imaging slice parameters.

Next, an explanation will be provided as to a method for calculating a position corresponding to the inclination reference point of the arbitrary subject, by the real imaging slice position calculator 220 using the imaging slice parameters. The real imaging slice position calculator 220 searches through the surrounding tissue on the scout image of the imaging target subject, assuming the proximity feature point extracted by the imaging slice position calculation algorithm as a starting point, and extracts a region coinciding with the pixel density pattern, thereby identifying the position. A specific procedure thereof will be described in the following.

Firstly, a tag of each proximity feature point being the imaging slice parameter is referred to, and according to the anatomical features extracted by the imaging slice position calculation algorithm, the associated proximity feature points (nx1', ny1') and (nx2', ny2') of the imaging target subject are extracted. Then, the distance NL' between the extracted proximity feature points is calculated.

Next, the center point of the micro-region image that is generated assuming the inclination reference point (x1, y1) as the center is moved in a circular region within the distance of A×NL1/NL×NL' from the proximity feature point (nx1', ny1') to perform matching process, and then a point (x1', y1') corresponding to the inclination reference point is extracted. Similarly, the center point of the micro-region image that is generated assuming the inclination reference point (x2, y2) as the center is moved within a circular region within the distance of A×NL2/NL×NL' from the proximity feature point (nx2', ny2') to perform matching process, and then a point (x2', y2') corresponding to the inclination reference point is extracted.

Here, the item "A" represents a real number at least 1, and 2 is assigned there to, for instance. In addition, the micro-region image used in the matching process is adjusted in such a manner that the imaging region is interpolated and expanded to NL'/NL and then the resolution of one pixel becomes equal to the image of the imaging target subject.

An amount of normalized mutual information, correlation coefficient, and the like, are used for the matching process, for instance. The micro-region image used in the matching process may be the image itself, a binary image thereof, or an image with edge enhancement by differentiation operations on the image. According to the aforementioned method, it is possible to identify the positions on the imaging target subject with a high degree of accuracy, the positions corresponding to the inclination reference points 422 and 423 that the user designates on the standard image.

It is to be noted that as for the central reference point 424, the imaging slice parameter is generated in the similar manner, and the center position of the real imaging slice position is calculated.

With this configuration, since the pattern matching corrects the displacement, it is possible to extract the points corresponding to the central reference point and the inclination reference points designated by the user, with a high degree of accuracy, on the position-locating image of the imaging target subject. Therefore, this may enhance the accuracy in calculating the real imaging slice position.

As explained above, there are multiple methods for calculating the imaging slice parameter, and those methods may be combined. Combining the methods may enhance the setting precision.

Here, as for the two inclination reference points 422 and 423 being designated, information indicating the following may be allowed to be inputted; whether the inclination determined by those points is parallel to the imaging plane or orthogonal to the imaging plane. With this configuration, this enables more detailed settings of the imaging slice position reference, and enhances the operability.

In addition, the designated two inclination reference points 422 and 423 and central reference point 424 may be defined in a device coordinate system, without establishing association with the anatomical features. It is further possible to configure such that any of the following is selectable; establishing association with the anatomical features, or defining the points in the device coordinate system. If the points are defined in the device coordinate system, processing of the anatomical features on the scout image becomes unnecessary. This configuration enables managing the case that imaging is required, for instance, focusing the center of the imaging slice on the target region with the inclination at a fixed angle in the device coordinate system.

It is further configured such that the standard image displayed in the image displaying region 323 of the user interface 301 is selectable by the user. In other words, the reference information accepting region 320 is further provided with an image designating region for accepting designation of the standard image that is displayed in the image displaying region 323. This configuration enables setting criteria of the imaging slice position, as to the standard imaging slices of various slices.

On this occasion, it is further possible to configure such that multiple standard images are registered in the storage device 112 in advance for each imaging site, and the user is prompted to select one out of those images. It is alternatively possible that the user is allowed to set arbitrarily a slice which is to be displayed as the standard image (slice image) for setting the reference information.

Figure 8:
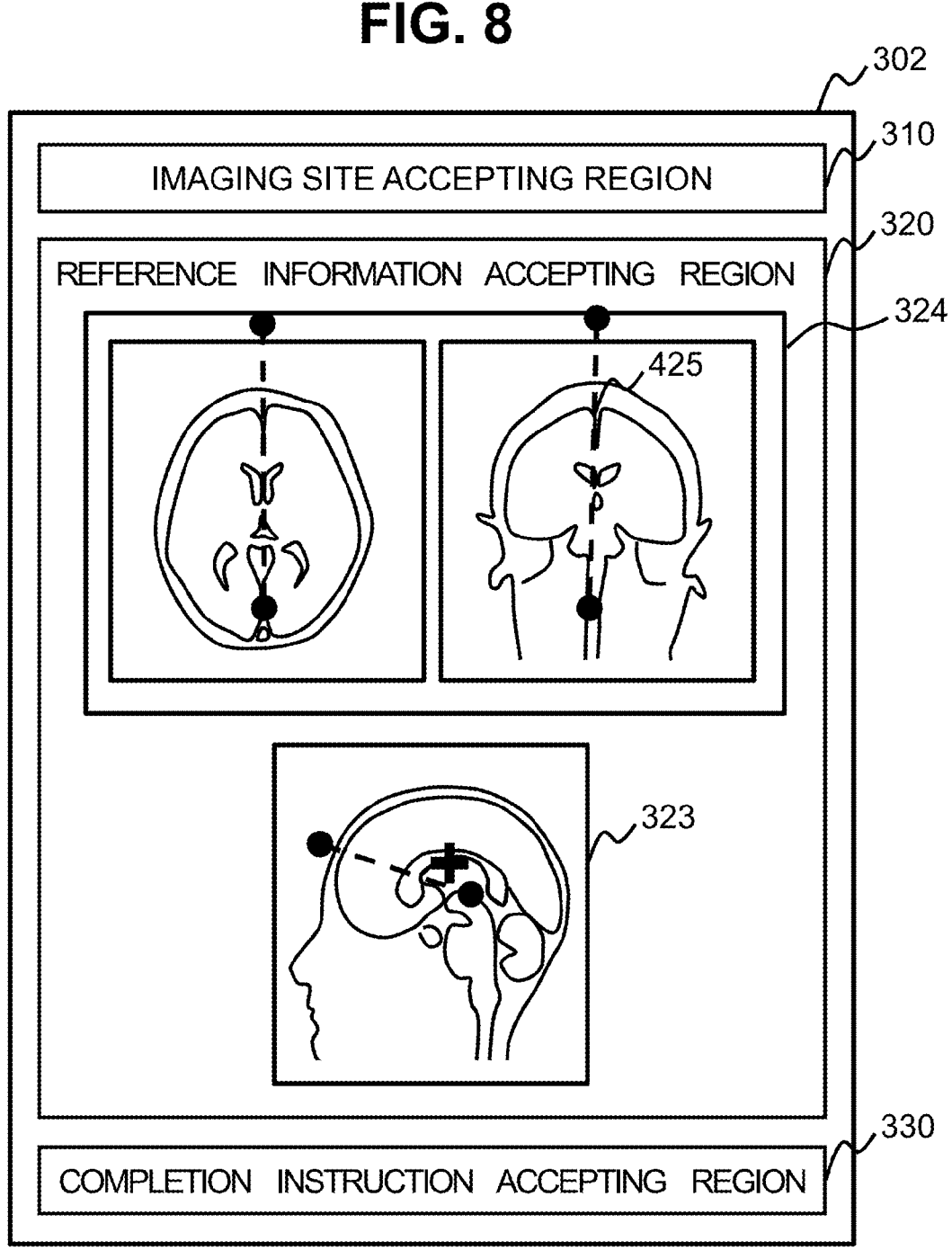
FIG. 8 illustrates another example of the user interface for accepting basic information according to the first embodiment.

FIG. 8 illustrates the user interface 302 in the case where the user sets an arbitrary slice. Similar to the user interface 301, the user interface 302 for this case is provided with the imaging site accepting region 310, the reference information accepting region 320, and the completion instruction accepting region 330. The imaging site accepting region 310 and the completion instruction accepting region 330 have the same functions as those having the same names in the user interface 301.

The reference information accepting region 320 is provided with the image designating region 324 where the user sets the slice (image) to be displayed, and the image displaying region 323 for displaying an image of the slice designated by the user.

The image designating region 324 is provided with at least one display region, and the axial slice of the standard image is displayed in each display region. Here, there is shown an example that two display regions are provided to display the transverse plane and the coronal plane. The user designates the slice 425 on the axial slice image that is displayed in the image designating region 324, the slice 425 corresponding to the image being displayed as the standard image, in the image displaying region 323.

The reference information acceptor 211 cuts out the slice accepted via the image designating region 324 as the standard image, and displays the slice in the image displaying region 323. By way of example, a method for cutting out the slice employs the MPR (Multi Planar Reconstruction) process of 3D image. The user configures the settings of the reference information on the standard image that is cut out and displayed in the image displaying region 323.

It is also possible to configure such that an imaging range is provided on the standard image that is displayed in the image displaying region 323. This configuration enhances visual effects, upon setting the imaging position by the user.

On this occasion, it is further possible to enable inputting of imaging parameters for specifying the imaging range, such as an FOV, the number of slices, and spacing between the slices, via the reference information accepting region 320. According to the parameters being accepted, the imaging range specified by the imaging parameters is displayed in the image displaying region 323. This configuration enables setting of the imaging slice position closer to the real position, thereby enhancing the operability.

It is further possible that multiple imaging ranges are allowed to be inputted, and the inclination reference points 422 and 423 and the central reference point 424 are settable for each imaging range. With this configuration, even in the examination that requires setting of multiple imaging sites such as interspinal discs of the spine, it is possible to set the reference information for each of the regions simultaneously, allowing the standard imaging slices to be set simultaneously.

It is to be noted that depending on the imaging site, setting of multiple imaging slice positions is required. In order to manage this kind of situation, the user interface may be configured in such a manner that multiple reference information accepting regions 320 and multiple completion instruction accepting regions 330 are provided. It is to be noted here that the number of those regions corresponds to the number of imaging slice positions that require the setting.

Upon accepting the imaging site via the imaging site accepting region 310, the reference information acceptor 211 generates and displays the user interface. The user interface being displayed is generated based on user interface screen data held in the storage device 112 in association with the region. On this occasion, the storage device 112 registers the necessary number of imaging slices, in association with the imaging sites. The reference information acceptor 211 generates the user interface in such a manner that the reference information accepting region 320 (image displaying region 323) and the completion instruction accepting region 330 are displayed, in response to the number of imaging slices registered in association with the accepted imaging sites.

Hereinafter, an explanation will be provided as to the example where the knees are assumed as the imaging site. When the imaging site corresponds to the knees, it is necessary to configure the settings of two imaging slice positions. Here, an explanation will be provided, as to the example where the reference information is accepted on the image. In other words, there will be explained the example that user interface is provided with two sets of following regions; the image displaying region 323 and the completion instruction accepting region 330.

Figure 9:
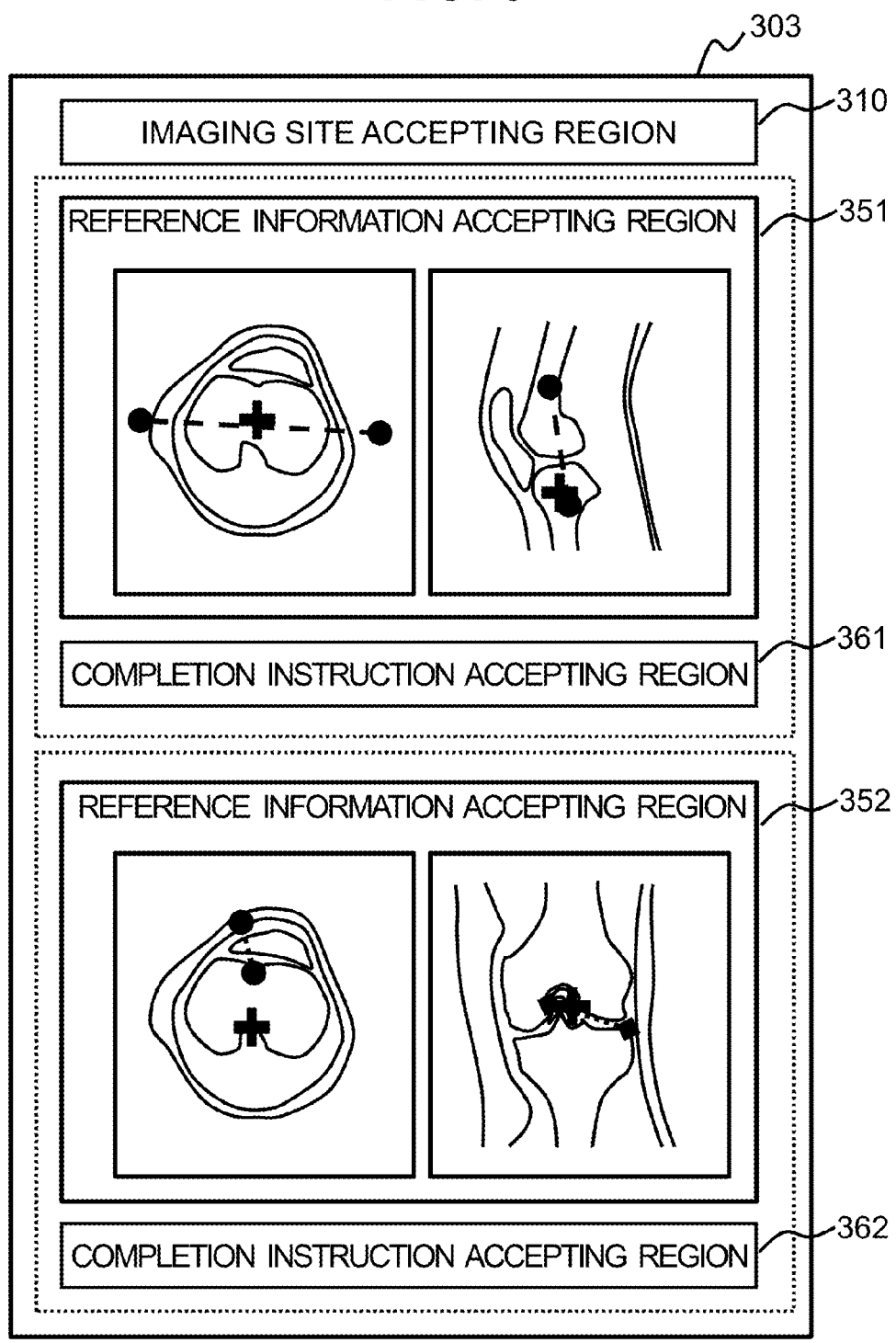
FIG. 9 illustrates another example of the user interface for accepting basic information according to the first embodiment.

FIG. 9 illustrates one example of the user interface 303 for this case. The user interface 303 is provided with the imaging site accepting region 310, the first image displaying region 351, the first completion instruction accepting region 361, the second image displaying region 352, and the second completion instruction accepting region 362.

Similar to the aforementioned user interface 302, in the first image displaying region 351, the standard image which is registered in the storage device 112 is displayed in association with the imaging site, in advance. The user inputs the reference information on the standard image, and sets the first standard imaging slice. When the reference information acceptor 211 accepts an input from the user via the first image displaying region 351 and the first completion instruction accepting region 361, the generator of imaging slice parameter 212 generates the first imaging slice parameter. The procedure for generating the first imaging slice parameter is similar to the aforementioned modification example.

In the second image displaying region 352, an image of the first standard imaging slice is displayed as the standard image. This image of the first standard imaging slice corresponds to a slice that is designated by the inclination reference points and the central reference point, on the standard image displayed in the first image displaying region 351. The user inputs the reference information on this standard image, and sets the second standard imaging slice. When the reference information acceptor 211 accepts an input from the user via the second image displaying region 352 and the second completion instruction accepting region 362, the generator of imaging slice parameter 212 generates the second imaging slice parameter. This procedure for generating the second imaging slice parameter is similar to the aforementioned modification example.

It is further possible to configure such that according to the user's selection, the image being the same as the standard image displayed in the first image displaying region 351 is also displayed in the second image displaying region 352. Alternatively, the standard image to be displayed in the second image displaying region 352 may be registered in advance.

Figure 10:
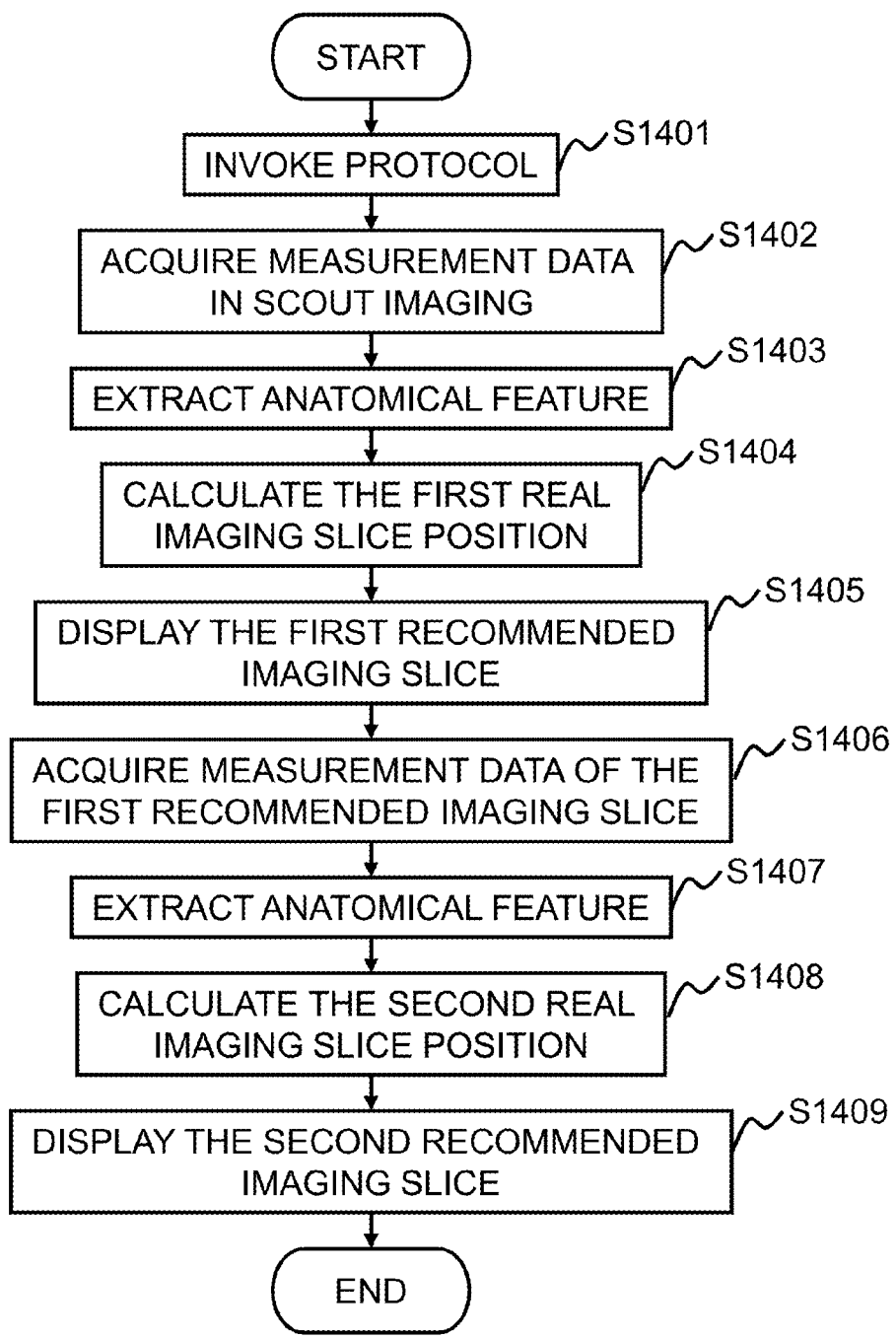
FIG. 10 is a flowchart showing a process from starting examination to the end of the real imaging slice position calculating process according to a modification example of the first embodiment.

Hereinafter, with reference to FIG. 10, a flow of the real imaging slice position calculating process according to the real imaging slice position calculator 220 will be explained, in the case of the region that requires setting of multiple imaging slices. In this example here, it is assumed that the first and the second standard imaging slices are already set, and registration of the slices into the protocol is completed.

Firstly, the computer 110 invokes the protocol (step S1401). Next, the computer 110 executes the scout imaging and acquires measurement data (step S1402). Next, the anatomical feature extractor 221 extracts the anatomical feature from the measurement data (step S1403). Next, the real imaging slice position calculator 220 refers to the first imaging slice parameter and calculates the first real imaging slice position by using the extracted anatomical feature (step S1404). Then, the display part 230 displays thus calculated first real imaging slice position on the monitor 111 as the first recommended imaging slice position to be shown to the user (step S1405). On this occasion, it is possible to configure such that the user is allowed to adjust the first recommended imaging slice position freely.

Next, the computer 110 executes imaging at the first recommended imaging slice position, and acquires the measurement data (step S1406). The imaging here may be the main scan of a diagnostic image, or it may be scout imaging. Next, the anatomical feature extractor 221 extracts the anatomical feature from the measurement data (step S1407). Then, the real imaging slice position calculator 220 refers to the second imaging slice parameter, and calculates the second real imaging slice position by using thus extracted anatomical feature (step S1408). Then, the display part 230 displays thus calculated the second real imaging slice position on the monitor 111, as the second recommended imaging slice position to be shown to the user (step S1409).

This configuration enables automatic setting of the real imaging slice position, in the same flow as the manual setting. In addition, since multiple imaging slice positions are set, three-dimensional imaging is not necessary, and recommended imaging slice positions are set according to only the very minimum two-dimensional imaging, so as to be shown to the user, expecting enhancement in measurement efficiency.

In the modification example above, setting of two imaging slices is taken as an example, but the number of imaging slices being set is not limited to two. The user interface may be configured as being provided with necessary number of slices, reference information accepting regions, and completion instruction accepting regions. In the second and the subsequent reference information accepting regions, since inputting of the reference information is previously accepted, the standard imaging slice that is specified by the reference information accepted immediately before, is displayed as the standard image.

In addition, in the second and the subsequent real imaging slice position calculating processes, the real imaging slice position has already been calculated, and therefore, the real imaging slice position calculator 220 uses the image at the real imaging slice position calculated immediately before, as the image for extracting the anatomical feature.

As discussed above, the reference information acceptor 211 accepts the reference information of multiple standard imaging slices, and if an input of the reference information is previously accepted, it is possible to assume the image of the standard imaging slice specified by the reference information accepted immediately before, as the standard image. Every time accepting the reference information via the reference information acceptor 211, the generator of imaging slice parameter 212 generates the imaging slice parameter from the reference information, and the real imaging slice position calculator 220 may assume as the scout image, the image of the real imaging slice position being calculated immediately before, in the case where the real imaging slice position is calculated previously.

It is to be noted that if multiple standard imaging slices are set for one imaging site, it is possible to configure such that any name is provided to the standard imaging slice (imaging slice parameter), being set by the standard imaging slice setter 210 and registered in the storage device 112. Then, upon generating the protocol, the user may be allowed to select the standard imaging slice to be calculated according to this name, for each pulse sequence in the main scan. In this case, the storage device 112 may store, together with the name of the standard imaging slice, the imaging slice position calculation algorithm to be executed, the imaging slice parameter to be used, and the like.

It is to be noted that in the present embodiment, the real imaging slice position calculator 220 uses the imaging slice position calculation algorithm being registered in advance in the storage device 112 to extract the anatomical feature and calculate the real imaging slice position. On this occasion, the imaging slice parameter is registered in the storage device 112 in advance. Then, the imaging slice position calculation algorithm refers to the imaging slice parameter registered in the storage device 112 upon performing the calculation, thereby implementing the real imaging slice position calculating process.

In other words, the MRI apparatus 100 of the present embodiment is further provided with a storing means for registering the imaging slice parameter being generated, the real imaging slice position calculator 220 may calculate the real imaging slice position according to the imaging slice position calculation algorithm being predetermined for each region, and the imaging slice position calculation algorithm may refer to the imaging slice parameter that is registered in the storing means upon performing the calculation.

With the configuration as described above, the MRI apparatus 100 of the present embodiment may control the storage capacity to the minimum, even in the case where the imaging slice parameter is increased.

However, the method for calculating the real imaging slice position according to the imaging slice position calculation algorithm is not limited to this example. By way of example, it is possible to configure such that every time the imaging slice parameter is generated, the imaging slice position calculation algorithm itself may be updated by using the imaging slice parameter. In other words, in the step S1107 of the standard imaging slice setting process, the calculated imaging slice parameter is used to update a program of the imaging slice position calculation algorithm for the imaging site, and the program is registered in the storage device 112 again.

Specifically, when the "lumbar vertebra" is accepted via the imaging site accepting region 310, the "centrum" is accepted via the anatomical feature accepting region 321, and the "sagittal plane" is accepted via the slice orientation accepting region 322, the program is rewritten in such a manner that the imaging slice position calculation algorithm for the lumbar vertebra calculates the real imaging slice position, at which the imaging center corresponds to the center of gravity of the centrum and the orientation of the imaging plane corresponds to the sagittal plane. Then, the rewritten imaging slice position calculation algorithm is registered in the storage device 112.

In other words, the real imaging slice position calculator 220 calculates the real imaging slice position according to the imaging slice position calculation algorithm being predetermined for each region, and every time the imaging parameter is generated, the imaging slice position calculation algorithm may be updated to the algorithm on which the imaging slice parameter is reflected.

With this configuration, after extracting the anatomical feature in the step S1208 of FIG. 5, it is possible to calculate the real imaging slice position by the imaging slice position calculation algorithm according to the rewritten program. Therefore, the time that is required for the algorithm to refer to the imaging slice parameter is not necessary any more, enabling higher speed calculation.

It is to be noted that in the present embodiment, the standard imaging slice is identified by setting the information for specifying both the center and the inclination of the standard imaging slice, but this is not the only example. There is an alternative configuration, such as setting only the information for specifying the center, or only the information for specifying the inclination, depending on the region.

In the case of multi-slice imaging, another configuration is possible such as setting not the center of the imaging range, but the center position in the slice direction of a slice particularly numbered. In this case, the reference information accepting region 320 is further provided with a slice designation region for designating a slice for setting the center position, and a position inputted as the information for specifying the center is assumed as the center position of the designated slice, so as to set the standard imaging slice, and reflect the information on the imaging slice parameter.

<Second Embodiment>

Next, the second embodiment to which the present invention is applied will be explained. In the present embodiment, a real imaging slice position is calculated according to a method similar to that of the first embodiment. Then, every time of calculation, extraction accuracy is judged, in extracting the anatomical feature that is extracted by the algorithm, and a result of the judgment is presented to the user.

Figure 11:
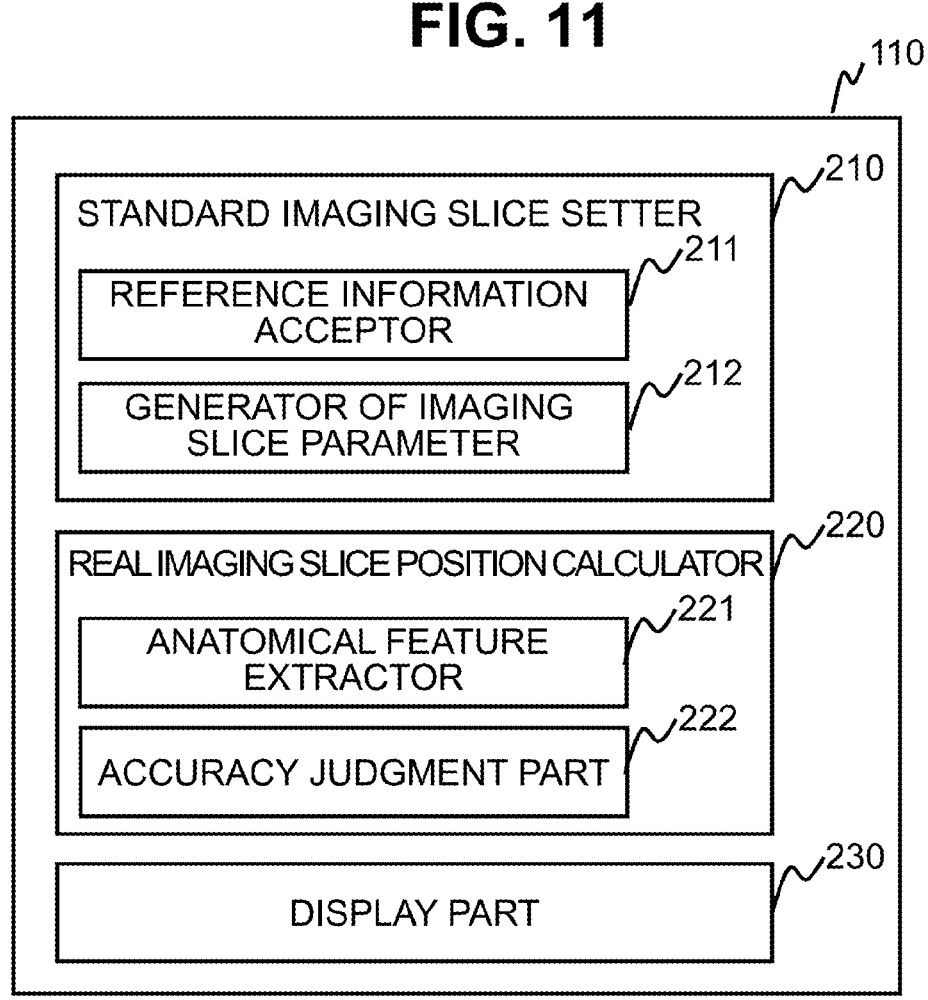
FIG. 11 is a functional block diagram of the computer according to the second embodiment.

The MRI apparatus 100 of the present embodiment has basically the same configuration as that of the first embodiment. However, in order to have the aforementioned function, the real imaging slice position calculator 220 of the present embodiment is further provided with the accuracy judgment part 222 for judging a degree of accuracy in extracting the anatomical feature, as shown in FIG. 11. In addition, the display part 230 shows the user the result of the judgment. In the present embodiment, when the result of judgment is low, the display part 230 displays an alert on the monitor 111. Hereinafter, an explanation will be provided, focusing on the configuration that is different from the first embodiment.

Figure 12:
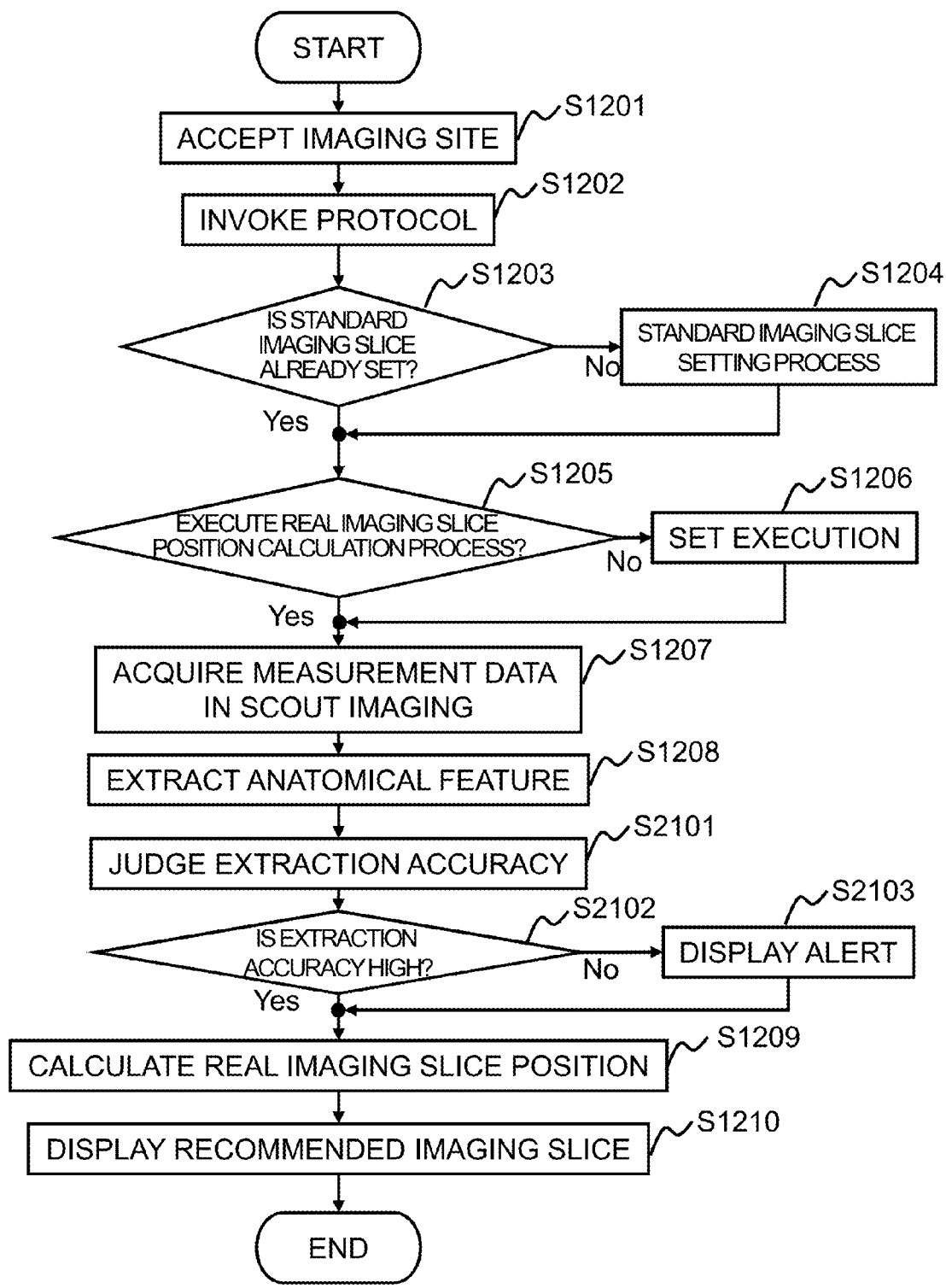
FIG. 12 is a flowchart showing a process from starting examination to the end of the real imaging slice position calculating process according to the second embodiment.

The standard imaging slice setting process by the standard imaging slice setter 210 is similar to that of the first embodiment. On the other hand, a flow of the real imaging slice position calculating process by the real imaging slice position calculator 220 is different. FIG. 12 illustrates a flow of the real imaging slice position calculating process by the real imaging slice position calculator 220 according to the present embodiment.

The processes from the step S1201 to the step S1208 are the same as the steps having the same reference numbers in FIG. 5. In the present embodiment, after extracting the anatomical feature according to the imaging slice position calculation algorithm (step S1208), the accuracy judgment part 222 judges the extraction accuracy of the anatomical feature being extracted (step S2101). The judgment is conducted according to a predetermined rule. The result of judgment is indicated by either of the following; high extraction accuracy representing that the extraction accuracy is equal to or higher than a predetermined accuracy, and low extraction accuracy representing that the extraction accuracy does not satisfy the predetermined accuracy. Details of the judgment will be described later. Then, upon achieving a high degree of extraction accuracy being equal to or higher than the predetermined accuracy, and the result of the judgment being determined as high extraction accuracy (step S2102), the process of the step S1209 in the first embodiment is performed.

On the other hand, if the predetermined extraction accuracy is not satisfied, and it is determined as low extraction accuracy, an alert is presented to the user (step S2103). It is sufficient that the alert indicates to the user that the extraction accuracy of the anatomical feature calculated by the real imaging slice position calculation algorithm does not satisfy the predetermined extraction accuracy. The alert may have any presentation form. It may be a display or a sound. After the alert indication, the process proceeds to the step S1209.

It is possible to configure such that after showing the alert in the step S2103, a predetermined temporary imaging slice position is presented to the user, without shifting to the step S1209. The temporary imaging slice position being predetermined may be an axial imaging position, for instance. When the user designates the tissue, the temporary imaging slice position may be an imaging slice position obtained by aligning the center of gravity of the tissue with the imaging center. With this configuration, it is possible to avoid that a recommended imaging slice position with a large positional error is obtained and presented to the user. Therefore, this may mitigate unnecessary operational loads on the user.

Methods for judging the extraction accuracy according to the accuracy judgment part 222 are as the following.

By way of example, in the first method, the extraction accuracy is judged by determining whether or not the imaging position of the image acquired for extracting the anatomical feature is appropriate.

Firstly, information regarding the center position and the orientation of the imaging site is acquired from the image that is acquired for extracting the anatomical feature. In the case of the head region examination, for instance, the information regarding the center position and the orientation may be the center position coordinates of the brain, and the position and the orientation of the midsagittal plane. In the case of the spine examination, the information may be the coordinates of the centrum or spinal nerves, and the like, in the axial image. In the case of the knee examination, the information may be the central coordinates of the thighbone. Approximate positions regarding those information items may be extracted according to an image analyzing process, based on a part of slice images in the imaging site, that is for example, a triaxial orthogonal slice image used when the imaging slice position is set manually.

Next, information regarding the center position and orientation of the imaging site is compared with the imaging region of the scout imaging. Next, it is calculated as a ratio in the scout region, whether or not the center position is included in the scout imaging region, or to what extent a predetermined plane region and the central axis of the imaging site defined by the center position and the orientation are included in the scout imaging region.

By way of example, as for the center position, if it is not included in the scout imaging region, it is determined that the extraction accuracy of the anatomical feature is low, and the result of judgment is outputted indicating low extraction accuracy. As for the plane region and the central axis, if the ratio included in the scout imaging region is equal to or less than 90%, it is determined that the extraction accuracy of the anatomical feature is low. Then, the result indicating low extraction accuracy is outputted. It is to be noted here that the ratio for the judgment is just an example and it is not limited thereto.

Specifically, a detailed explanation will be provided, for example, as to the case where features of the head region are extracted by using a two-dimensional multi-slice image of each of the transverse plane, coronal plane, and sagittal plane. In the example here, during the scout imaging, in order to reduce the imaging time, a slice image passing in proximity to the brain center is acquired on each of the planes, allowing an anatomical structure of the brain to be figured out, without acquiring data of the overall head region. Generally, since the scout image is taken at a predetermined imaging position in the device coordinate system, the imaging position is adjusted upon setting the subject so that a slice image passing through the brain center is acquired. However, there is a possibility that the subject moves during the period from the time of completion of setting to the time of scout imaging, and a slice image of a targeted brain center may not be obtained in the scout imaging.

In this case, the coordinates of the brain center are extracted from the scout image being acquired according to the image processing. If it is judged that the extracted coordinates of the brain center are included in the scout imaging region, the image under analysis is determined to be the slice image passing in proximity to the targeted brain center. If the coordinates of the brain center are not included in the scout imaging region, it is not possible to extract the anatomical feature from the scout image under analysis, and it is determined that the extraction accuracy is deteriorated significantly. Therefore, also in this case, the result indicating low extraction accuracy is outputted.

The anatomical structure assumed as a reference for setting the imaging slice position in the head region is extracted by analyzing the slice image in the midsagittal plane. Therefore, by judging whether or not the midsagittal plane is included in the imaging region of the scout image, it is possible to predict the deterioration of the extraction accuracy in the similar manner. In other words, if the midsagittal plane is not included in the scout imaging region, the result indicating low extraction accuracy is outputted.

In the second method, extraction of the anatomical feature is executed according to multiple means, and the extraction accuracy is judged depending on a degree of coincidence of the extraction results from the respective means. A detailed explanation will be provided, taking an example that the extraction accuracy is judged as to the median line in the axial image of the head region.

In the case where the image to be analyzed is T1-weighted image, the pixel value on the median line is low relative to the surrounding cerebral parenchyma. Therefore, in order to extract the median line on the axial image, a black linear portion is retrieved. In other words, conditions for retrieving the median line are set as follows; 1) a region where the sum total of the image values on a straight line is low in the brain region, 2) a region where the sum total of the second derivatives is high in the direction vertical to the straight line at a point on the straight line in the brain region, and the like, and then the median line is extracted. On this occasion, the midsagittal plane is a plane for dividing left and right. Thus, the tissue is symmetric with respect to the midsagittal plane. Accordingly, in addition to the aforementioned conditions for retrieving the median line, following may also be assumed as the conditions; 3) a straight line portion being close to the center of gravity coordinate of the brain, and 4) a portion in the brain region, in which as for the pixel values in the direction vertical to the straight line, there is a high correlation coefficient between the pixel value being inverted on one side of both sides of the straight line and the pixel value on the other side, and the like. For specifying a portion being the most suitable for each of the above conditions, evaluation values are calculated, such as a total sum of the pixel values on the straight line for the condition 1), a total sum of the second derivatives on the straight line for the condition 2), a distance between the brain center and the straight line for the condition 3), and the correlation coefficient between the left and right for the condition 4), thereby extracting a portion where a minimum value or a maximum value of the evaluation value is obtained.

Here, if a region that is the most suitable only for one condition is extracted as the median line, it is more likely that an error occurs in extraction. By way of example, under the condition 1), a low-signal portion on the corpus callosum may be recognized as the median line. Under the condition 3), the straight line passing through the brain center in any direction may be assumed as the midsagittal plane. If the transverse plane is imaged with the head region being inclined, there is a possibility the median line may be displaced from the center. Under the condition of 4), a straight line dividing into an upper portion and a lower portion having a relatively high symmetric property may be recognized as the median line erroneously.

In order to specify a portion that is suitable for multiple search conditions, each evaluation value is standardized by the maximum value, and the like. Thereafter, an evaluation value of a combined condition in which a smaller value indicates suitability for the condition is obtained according to the four arithmetic operations, and the portion having the minimum evaluation value is extracted as the median line. This configuration may enhance the robustness of the process for extracting the midsagittal plane, and increase the extraction accuracy.

It is to be noted that if the portion extracted by the evaluation value of a single condition entirely agrees with the portion extracted by the evaluation value of the combined condition, reliability of thus extracted median line is high. Therefore, in this case, the extraction accuracy is determined to be high, and the result indicating high extraction accuracy is outputted. However, by way of example, if a portion different from the portion extracted by the combined condition, is extracted in two conditions out of the four conditions, it is predicted that the reliability of the extraction accuracy is deteriorated. Therefore, in this case, the result indicating low extraction accuracy is outputted.

Alternatively, it is possible to configure such that a threshold is set to the evaluation value that is calculated under the combined condition, and if the evaluation value is equal to or larger than the threshold, it is determined that the extraction accuracy is low, and the result indicating low extraction accuracy is outputted. As a method for determining the threshold, for example, the evaluation values of past examples; a successful example and a failed example for extracting the median line are referred to, and an average value of those evaluation values is determined as the threshold.

In the third method, the extraction accuracy is determined according to the degree of coincidence between the shape of the surrounding tissue of the extracted anatomical feature and the shape of the surrounding tissue of a standard anatomical feature stored in the database. An explanation will be provided, taking an example that the anatomical feature is extracted on the midsagittal plane image.

Firstly, an image of a small field of view centering on the anatomical feature being a target for extraction in the standard midsagittal plane image is stored in the database. The small field of view is set as 20 mm ×20 mm, for instance, in the case of the midsagittal plane image, and as for other regions, the field of view is set in such a manner as being appropriate for the region. Next, after extracting the anatomical feature by the feature point extraction algorithm, such as the Active Shape Model, the correlation coefficient is calculated between the image of the small field of view centering on the extracted feature structure, and the image stored in the database, and the number of the anatomical features whose correlation coefficient is equal to or less than 0.8 is counted. In the case where the number of anatomical features being counted is three or more, it is determined that the extraction accuracy of the anatomical feature is low, and the result indicating low extraction accuracy is outputted. It is to be noted that the value of the correlation coefficient and the count number being the threshold are just examples, and those are not limited thereto.

In the fourth method, the size and the orientation of the target region are calculated based on the extracted anatomical feature, being checked against anatomical insight, thereby judging the extraction accuracy. An explanation will be provided, taking an example that the anatomical feature is extracted in the midsagittal plane image.

The head length (length from the middle of the forehead to the back of the head) is approximately 190 mm, as an average value of adult males. Therefore, if the head length calculated from the extracted anatomical feature is equal to or longer than 220 mm, for instance, it is determined that the feature extraction accuracy is low, and the result indicating low extraction accuracy is outputted. It is possible to configure such that the head length assumed as the threshold is changed based on male or female, race, or the like.

Since movement of the head region is restricted in the state being set on the head region coil, it is conceivable that the tilt of the head region falls into the range approximately from −45 degrees to 60 degrees. Therefore, the tilt is calculated based on the extracted anatomical feature, for instance, the angle of the corpus callosum, or the like, and if the tilt does not fall into the range being set, it is determined that the extraction accuracy is low, and the result indicating low extraction accuracy is outputted.

As explained above, as for the MRI apparatus 100 of the present embodiment, the real imaging slice position calculator 220 of the MRI apparatus 100 in the first embodiment is further provided with the accuracy judgment part 222 for judging the degree of the extraction accuracy of the anatomical feature extracted by the anatomical feature extractor 221, and if the result of judgment by the accuracy judgment part 222 is low, an alert may be displayed on the monitor.

Both the accuracy of the reference information set by the user and the calculation accuracy of the imaging slice position calculation algorithm, exert influence on the imaging slice position that is presented by the user according to the method of the first embodiment. In the present embodiment, the extraction accuracy of the anatomical feature is judged, with regard to the accuracy in calculating the real imaging slice position according to the imaging slice position calculation algorithm, and thus this enables presenting to the user, the accuracy of the imaging slice position calculation algorithm. Therefore, the user is allowed to determine whether or not it is necessary to readjust the reference information. According to the present embodiment, since the accuracy information as to the imaging slice position calculation algorithm is allowed to be presented to the user, this may restrain occurrence of unnecessary works and enhance the operability.

<Third Embodiment>

Next, an explanation will be provided as to the third embodiment to which the present invention is applied. In the present embodiment, a real imaging slice position is calculated according to a method similar to the method of the first embodiment. Then, adjustments accepted from the user as to the calculated real imaging slice position is stored as learning data, and the learning data is fed back to the imaging slice parameter.

The MRI apparatus 100 of the present embodiment has basically the same configuration as that of the first embodiment. It is to be noted here that since the computer 110 in the MRI apparatus 100 of the present embodiment has the aforementioned function, it is further provided with a configuration for storing as learning data, the adjustments accepted from the user after presenting the recommended imaging slice position, and updating the imaging slice parameter. Hereinafter, an explanation will be provided, focusing on the configuration that is different from the first embodiment.

Figure 13:
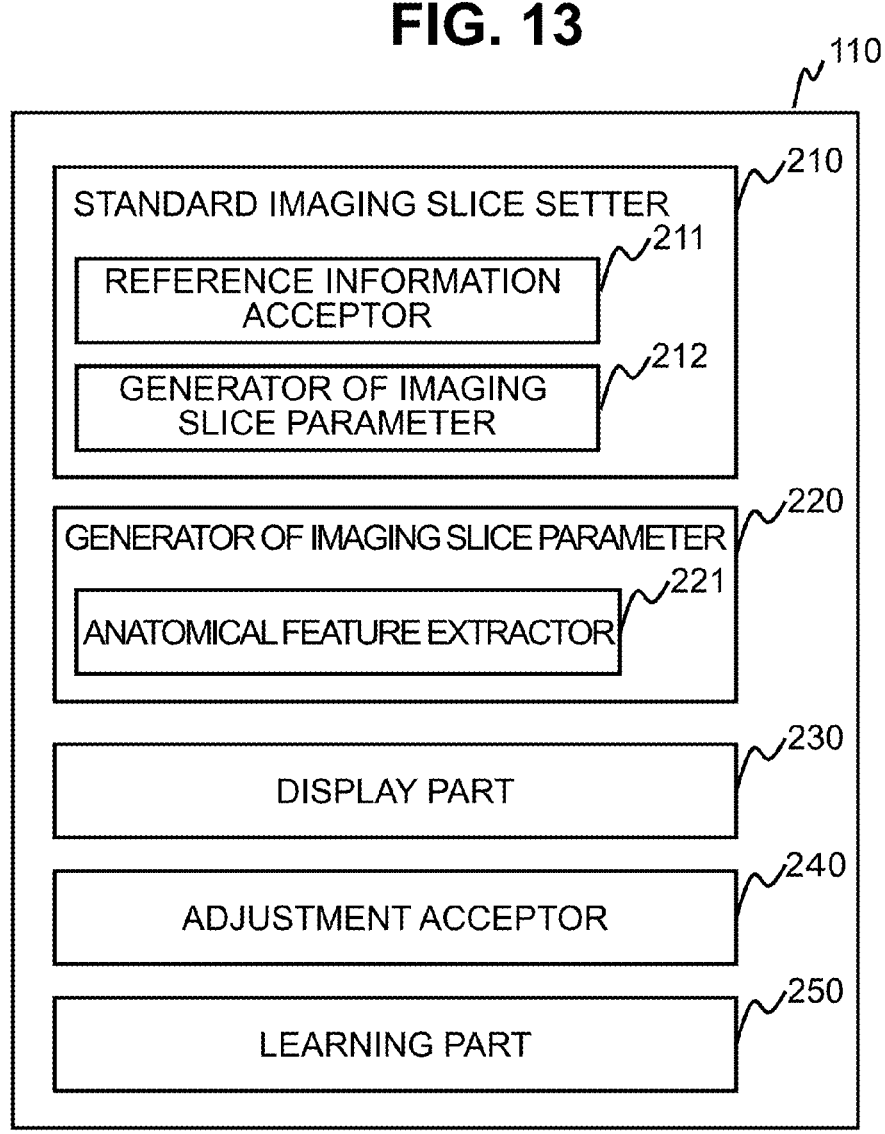
FIG. 13 is a functional block diagram of the computer according to the third embodiment.

FIG. 13 is a functional block diagram showing the computer 110 of the present embodiment. The computer 110 of the present embodiment implements, in addition to the standard imaging slice setting process, the real imaging slice position calculating process, and the recommended imaging slice presenting process, as explained in the first embodiment, a process for accepting adjustments from the user, a process for registering the adjustments being accepted as learning data in the storage device 112, and a feedback process for analyzing the learning data and feeding the learning data back to the imaging slice parameter or to the imaging slice position calculation algorithm. In order to implement the processes above, the computer 110 of the present embodiment incorporates an adjustment acceptor 240 and a learning part 250, in addition to the functions provided in the computer 110 of the first embodiment.

As described above, the adjustment acceptor 240 of the present embodiment accepts an adjustment from the user to the real imaging slice position calculated by the real imaging slice position calculator 220, being the recommended imaging slice position presented to the user, and registers the adjustment in the storage device 112 as learning data. The registration is performed in association with the imaging site. Furthermore, the learning part 250 analyzes the adjustments (learning data) being accepted, and feeds the result back to the imaging slice parameter.

Following is a procedure of the feedback. When the user makes adjustment via the adjustment acceptor 240, the learning part 250 uses a final central reference point of the imaging target subject (imaging center coordinate of the imaging target subject) obtained by the user's adjustment, and the coordinates of the anatomical features being associated, to solve the system of equations of the formula (4), and then new shape functions, $N_1$, $N_2$, $N_3$, and $N_4$ are obtained. According to the final inclination reference point obtained by the user's adjustment and the associated coordinates of the anatomical features of the subject, the aforementioned formula (1) is used to calculate the standardized difference values dx1, dy1, dx2, and dy2. Then, the imaging slice parameter is updated by thus obtained shape functions and the standardized difference values.

It is further possible to configure such that the learning is performed for each subject. In other words, upon accepting the adjustment from the user and obtaining new shape functions and standardized difference values, the imaging slice parameter is not updated, but it is newly registered as the imaging slice parameter of the subject, in association with the subject. Only when new shape functions and standardized difference values are obtained for the same subject, the imaging slice parameter of the subject is updated.

It is to be noted that in the above example, there has been explained a method for updating the shape functions and the standardized difference values being stored as the imaging slice parameters, by using the learning data (adjustments), but this is not the only example. By way of example, it is possible to configure such that the learning data is reflected on the selection of the proximity feature point and reference feature point.

In this case, the standardized difference values and the shape functions are registered in association with various combinations of proximity feature points and various groups of reference feature points, respectively. Then, among those registered items, a combination of proximity feature points and a group of reference feature points with the least adjustments by the user are decided.

A detailed explanation will be provided as to a method for analyzing the learning data by the learning part 250 for this case.

In the first embodiment, a group of the reference feature points as a base for calculating the shape function is predetermined. On the other hand, in the present embodiment, all the combinations of the number of the reference feature points that are necessary for calculating the shape function are extracted from all the extractable anatomical features, and the shape function for each combination is calculated and stored.

By way of example, the number of the anatomical features extracted in the imaging process is assumed as N, and the number of the anatomical features (the number of reference features) used for interpolation is assumed as M. In this case, the number of the combinations P of the reference feature points is calculated according to the formula (6):

$$P = {}_N C_m \qquad (6)$$

Here, upon calculating the imaging slice parameter based on the central reference point 424, the shape functions $N_1$, $N_2$, $N_3$, and $N_4$ being the calculation information are obtained for each of the P combinations of the reference feature points.

The learning part 250 sets the combination of the reference feature points that may be the closest to the central reference point of the subject after the user's adjustments, as the combination of the reference feature points to be used for calculating the imaging slice parameter of the next subject. Hereinafter, an explanation will be provided as to the flow of examination including the process by the learning part 250. It is to be noted that an initial value of the combination of the reference feature points (a combination for calculation) used by the real imaging slice position calculator 220 is predetermined, among the P-way combinations of the reference feature points.

Firstly, the real imaging slice position calculator 220 calculates the central reference point of the imaging target subject, by using the combination for calculation of the reference feature points, and the shape function obtained by the combination for calculation, and presents the central reference point to the user. Then, the learning part 250 accepts the adjustment of the central reference point from the user.

On the other hand, the learning part 250 calculates the central reference point of the imaging target subject, as to each of all the (P-1) combinations of the reference feature points except the combination for calculation. Then, as to each of the central reference points being calculated, distance L from the central reference point after accepting the user's adjustment is calculated and it is registered in the storage device 112 as the learning data. Registration of the learning data is performed for each combination, by adding the data to a value of the distance registered in association with the combination. As for the combination for calculation, the distance L corresponding to the adjustment is registered (added). Then, the learning part 250 sets the combination of the reference feature points having the least distance value after the addition, among the registered learning data, as the combination for calculation.

The aforementioned process is repeated for each examination. In other words, as for the next subject, the real imaging slice position calculator 220 uses the combination for calculation that is assumed as the combination of the reference feature points with the shortest distance L in the previous imaging, so as to calculate the central reference point of the subject. In addition, the learning part 250 uses the combinations other than the combination above, to calculate the central reference point of the subject, and compares the result with the central reference point after the user's adjustment. Then, the learning part 250 calculates the distance L as to each combination, and adds the distance to the learning data, thereby updating the learning data. In addition to that, the combination for calculation is also updated.

As thus described, according to the present embodiment, the learning data is accumulated and updated for each examination. In other words, if the examination target is the K-th subject, the learning data is obtained after the addition of data for K times as to each combination. As for the second and the subsequent subjects, a combination of the reference feature points having the least added value of the learning data, and the shape function obtained therefrom are used as the imaging slice parameters, and the coordinate of the central reference point of the subject is calculated and presented to the user. This configuration enables calculation of the real imaging slice position with a higher degree of accuracy, and it is presented to the user as the recommended imaging slice position.

The proximity feature point that is used upon deciding the imaging slice parameter from the inclination reference point, may be treated in a similar manner. It is to be noted that as for the proximity feature point, predetermined multiple combinations are used, not all the combinations, out of a certain number of anatomical features in proximity to each of the reference points set by the user as the inclination reference points 422 and 423. It is possible to configure such that the combination to be used is set by the user. It is alternatively possible to use all the anatomical features within the range of a predetermined region centering on each of the inclination reference points.

The method for reflecting the adjustments according to the learning part 250 is the same as the aforementioned case of the central reference point. In other words, a combination where the accumulated value of the distance is the minimum, between the inclination reference point of the subject obtained from each combination and the inclination reference point after the adjustment, is used upon calculating the real imaging slice position of the next subject.

As explained above, the MRI apparatus 100 of the present embodiment may further be provided with the adjustment acceptor 240 for accepting as the learning data, the adjustment of the imaging slice position calculated by the real imaging slice position calculator 220, and the learning part 250 for analyzing the learning data being accepted and feeding the learning data back to the imaging slice parameter, in addition to the MRI apparatus 100 of the first embodiment.

As described above, according to the present embodiment, there are provided the adjustment acceptor 240 for accepting the adjustments of the real imaging slice position calculated by the real imaging slice position calculator 220, and the learning part 250 for analyzing the accepted learning data and feeding the learning data back to the imaging slice parameter. Therefore, according to the present embodiment, since the adjustments by the user is reflected on the imaging slice parameter, this may allow setting of the standard imaging slice, in a manner more suitable for the user's purpose. This configuration enables calculation of the real imaging slice position with a higher degree of accuracy, and presenting the recommended imaging slice position that matches the user's needs.

It is to be noted that in the present embodiment, the combination of the anatomic features used for the calculation is updated based on the result of the adjustment of the first subject, but this is not the only example. It is further possible to configure such that the updating is performed after obtaining results of the adjustment as to a certain number of subjects or more. By way of example, the combination may be updated, after acquiring data of 10 subjects. With this configuration, variations of the calculated learning data due to the subject is restrained.

In order to mitigate the variations of the inclination reference point and the central reference point of the subject in the calculation due to the learning data, it is further possible to configure such that the feedback according to the learning data is stopped, after analysis and reflection of the learning data are completed with regard to a certain number of data items. The number of analysis until stopping the feedback may be configured as being predetermined, or designated by the user.

In the aforementioned embodiment, the learning data is updated by adding the latest result on the learning data, but this is not the only method for updating. It is possible to configure such that the learning part 250 calculates an average value between the latest learning data and already existing learning data every time the latest learning data is obtained, and this average value is registered. On this occasion, updating is performed assuming a combination of the reference points that render the average value to be a minimum, as the combination for calculation. It is further possible to configure such that the learning part 250 calculates, in addition to the average value, a standard deviation of the distance L computed for each examination, and this standard deviation is registered. On this occasion, updating may be performed assuming a combination of the reference points that render the standard deviation to be a minimum, as the combination for calculation, and further, the average value of the distance L in this combination is reflected as a correction amount for the imaging slice parameter. Accordingly, this configuration may enable presentation of a stable result with a high degree of accuracy and less variations.

It is to be noted that when the central reference point and the inclination reference point are calculated on the X coordinate and Y coordinate, a combination of the anatomical features to be used may be changed, upon calculation on each of the coordinates. By way of example, in the case of the central reference point, distance LX on the X coordinate and distance LY on the Y coordinate are calculated, and updating on each coordinate is performed by addition, and the like.

It is further possible to configure such that the learning data is categorized and stored, according to the age, sex, race, and the like, of the subject. With this configuration, the learning data is able to be reflected more effectively on the calculation of the real imaging slice position, expecting enhancement of accuracy.

In the present embodiment, an explanation has been made taking an example that the configuration of the first embodiment is provided with the adjustment acceptor 240 and the learning part 250, but this is not the only example. The configuration of the second embodiment may be provided with those functions.

<Fourth Embodiment>

Next, the fourth embodiment to which the present invention is applied will be explained. Some examinations (imaging) may require to set a position (related position) relating to the imaging slice position, independent of the imaging slice position. In the present embodiment, based on a position reference set by the user, both the real imaging slice position and a related position are set.

The related position may be a saturation region, an imaging region of navigator echoes, or the like, for instance.

The MRI apparatus 100 of the present embodiment has basically the same configuration as that of the first embodiment. As shown in FIG. 14, in order to have the aforementioned function, the computer 110 of the MRI apparatus 100 of the present embodiment is provided with a related position reference setter 260 for setting as a standard related position, a position relating to the imaging slice position being independent of the imaging slice position, and generating a related position parameter from thus set standard related position, and a real related position calculator 270 for calculating a real related position being the related position in the imaging target subject based on the related position parameter, in addition to the configuration of the first embodiment. Hereinafter, an explanation will be provided as to the present embodiment, focusing on the configuration different from the first embodiment.

The related position reference setter 260 performs basically the same processing as the standard imaging slice setter 210 of the first embodiment. In other words, the related position reference setter generates a user interface for accepting inputs from the user regarding the imaging site and the information being the reference for calculating the related position (related position reference), and displays the user interface on the monitor 111. Upon accepting the setting of the related position reference from the user via the user interface, a parameter (related position parameter) is calculated for obtaining the related position, based on the accepted related position reference and the related anatomical feature.

The storage device 112 holds data for generating the user interface. The storage device 112 also registers the related position parameter being calculated.

It is possible to configure such that as the related position reference, not only the reference for calculating the position but also an application purpose of the related position is able to be designated, such as a saturation region, and an imaging region of navigator echoes, for instance. As another configuration, multiple related positions may be settable. Additionally, the user may be allowed to input the reference information and the related position reference for setting the standard imaging slice, on the same user interface.

The real related position calculator 270 of the present embodiment performs basically the same processing as the real imaging slice position calculator 220 of the first embodiment. In other words, on the basis of the related position parameter, the related position reference in association therewith is calculated as to each imaging target subject, so as to decide a real related position being the related position on the imaging target subject.

As explained above, the MRI apparatus 100 of the present embodiment is provided with the related position reference setter 260 for setting as the standard related position, a position relating to the imaging slice position, being independent of the imaging slice position, and generating a related position parameter from the standard related position being set, and a real related position calculator 270 for calculating the real related position from the related position parameter, as the related position in the imaging target subject, in addition to the MRI apparatus 100 of the first embodiment.

As discussed so far, according to the present embodiment, it is possible to support setting not only the real imaging slice position, but also other related position necessary for the imaging, such as the saturation region and the imaging region of navigator echoes, for instance. Therefore, this enhances the operability.

It is to be noted that the present embodiment has been explained on the basis of the configuration of the first embodiment, but this is not the only example. It may be the configuration of the second embodiment or the third embodiment, which is provided with the configuration specific to the present embodiment as described above.

It is to be noted that in each of the embodiments, the computer 110 is provided with a CPU, a memory, the storage device, and the like, and the computer 110 implements each function by allowing the CPU to load in the memory the programs stored in the storage device, and execute the programs. All the functions or a part thereof may be implemented by a general-purpose information processor that is installed separately from the MRI apparatus 100, being capable of transmitting data to and receiving data from the MRI apparatus 100.

Each of the embodiments above takes the MRI apparatus as an example, but this is not the only example. Any imaging apparatus is applicable, if it is capable of imaging any plane in the three-dimensional space.

Explanation of References

100: MRI apparatus, 101: magnet, 102: gradient coil, 103: subject, 104: sequencer, 105: gradient magnetic field power supply, 106: radio frequency magnetic field generator, 107: RF coil, 108: RF probe, 109: receiver, 110: computer, 111: monitor, 112: storage device, 113: shim coil, 114: shim power supply, 116: input device, 210: standard imaging slice setter, 211: reference information acceptor, 212: generator of imaging slice parameter, 220: real imaging slice position calculator, 221: anatomical feature extractor, 222: accuracy judgment part, 230: display part, 240: adjustment acceptor, 250: learning part, 260: related position reference setter, 270: real related position calculator, 300: user interface, 301: user interface, 302: user interface, 303: user interface, 310: imaging site accepting region, 320: reference information accepting region, 321: anatomical feature accepting region, 322: slice orientation accepting region, 323: image displaying region, 324: image designating region, 330: completion instruction accepting region, 351: image displaying region, 352: image displaying region, 361: completion instruction accepting region, 362: completion instruction accepting region, 421: anatomical feature, 422: inclination reference point, 423: inclination reference point, 424: central reference point, 425: slice

What is claimed is:

1. A medical imaging apparatus capable of imaging any slice in three-dimensional space comprising:
    a standard imaging slice setter for obtaining a standard imaging slice associated with an imaging site, and generating one or more parameters for the imaging site, wherein the standard imaging slice setter automatically sets an imaging slice representing a typical imaging slice of the imaging site, the standard imaging slice setter comprising:
    a reference information acceptor for receiving at least one input including reference information associated with an anatomical feature for specifying the standard imaging slice; and
    a generator of the one or more parameters for the imaging site, wherein the one or more parameters are generated by associating the reference information with an anatomical feature including one or more feature points of the anatomical feature; and
    a real imaging slice position calculator for, automatically and without manual intervention, calculating a real imaging slice position for the imaging site by using a scout image based on both the one or more parameters and the identifying information of the anatomical feature, wherein the one or more parameters are generated before the real imaging slice position is calculated, and wherein the real imaging slice position calculator further comprises:
    an anatomical feature extractor for receiving the one or more parameters generated by the standard imaging slice setter, extracting the anatomical feature on the scout image and calculating the real imaging slice position based on the one or more feature points of the anatomical feature; and
    a display part for displaying to a user, the calculated real imaging slice position, as a recommended imaging slice,
    wherein the reference information acceptor accepts as the reference information the at least one input associated with the anatomical feature as information for specifying a center of the standard imaging slice, and a designation of two inclination reference points for specifying an inclination of the standard imaging slice, and
    wherein the generator of the one or more parameters determines reference anatomical feature points and calculates, as parameters, weights of the reference anatomical feature points, and a normalized value of a distance between each inclination reference point and the anatomical feature in proximity thereto.

2. The medical imaging apparatus according to claim 1, wherein,
    the reference information acceptor comprises an imaging site acceptor for accepting a first input of the imaging site, and a second input of the reference information based on information that is indicated depending on the imaging site accepted by the imaging site acceptor.

3. The medical imaging apparatus according to claim 2, wherein,
    the reference information acceptor displays a standard image of the imaging site accepted by the imaging site acceptor and accepts an input of the reference information on the standard image.

4. The medical imaging apparatus according to claim 3, wherein, the reference information acceptor accepts a designation of a particular one reference point on the standard image, as the information for specifying the center of the standard imaging slice in the reference information, and
    an imaging slice parameter generator generates the imaging slice parameter from the anatomical feature being predetermined and calculation information for calculating the reference point from the anatomical feature.

5. The medical imaging apparatus according to claim 4, wherein,
    the reference information acceptor further comprises a slice designation part for designating an imaging slice, and
    a center of the one reference point is set as the center of the imaging slice being accepted by the slice designation part among the standard imaging slice.

6. The medical imaging apparatus according to either of claim 3, wherein,
    the reference information acceptor accepts a designation of particular two reference points on the standard image, as information for specifying the inclination of the standard imaging slice in the reference information, and
    an imaging slice parameter generator generates an imaging slice parameter from the anatomical features respectively in proximity to the reference points, and calculation information for calculating the reference points from the anatomical features.

7. The medical imaging apparatus according to claim 6, wherein,
    the calculation information is a shape function.

8. The medical imaging apparatus according to claim 6, wherein,
    the calculation information is a tissue structure pattern surrounding the reference point.

9. The medical imaging apparatus according to claim 3, wherein,
    the reference information acceptor further comprises an image designation part for accepting a designation of an image to be displayed as the standard image, and
    the reference information acceptor displays the image designated by the image designation part as the standard image.

10. The medical imaging apparatus according to claim 3, wherein,
    the reference information acceptor accepts the reference information of the standard imaging slice being more than one, and
    if a previous input of the reference information is accepted, an image of the standard imaging slice specified by the reference information accepted immediately before is assumed as the standard image.

11. The medical imaging apparatus according to claim 10, wherein,
the generator of imaging slice parameter generates the imaging slice parameter from the reference information, every time accepting the reference information via the reference information acceptor, and
if the real imaging slice position is calculated previously, the real imaging slice position calculator assumes an image at the real imaging slice position calculated immediately before, as the scout image.

12. The medical imaging apparatus according to claim 3, wherein,
the reference information acceptor comprises an imaging parameter acceptor for accepting an input of an imaging parameter that specifies an imaging range, and
the reference information acceptor displays the imaging range specified by the imaging parameter on the standard image, according to the imaging parameter accepted by the imaging parameter acceptor.

13. The medical imaging apparatus according to claim 1, wherein,
the reference information acceptor accepts the at least one input associated with the anatomical feature, as information for specifying a center of the standard imaging slice, the information being included in the reference information.

14. The medical imaging apparatus according to claim 1, wherein,
the reference information acceptor receives a designation of orientation, as information for specifying an inclination of the standard imaging slice, the information being included in the reference information, and
an imaging slice parameter setter sets the orientation accepted by the reference information acceptor as an imaging slice parameter.

15. The medical imaging apparatus according to claim 1, further comprising,
a storage for registering the imaging slice parameter being generated, wherein,
the real imaging slice position calculator calculates the real imaging slice position according to an imaging slice position calculation algorithm that is predetermined for each region, and
the imaging slice position calculation algorithm refers to the imaging slice parameter that is registered in the storage upon calculation.

16. The medical imaging apparatus according to claim 1, wherein,
the real imaging slice position calculator calculates the real imaging slice position according to an imaging slice position calculation algorithm that is predetermined for each region, and
the imaging slice position calculation algorithm is updated to the imaging slice position calculation algorithm on which the imaging slice parameter is reflected, every time the imaging slice parameter is generated.

17. The medical imaging apparatus according to claim 1, wherein,
the real imaging slice position calculator further comprises an accuracy judgment part for judging a degree of accuracy of the anatomical feature extracted by the anatomical feature extractor, and
if a result of judgment by the accuracy judgment part is low, an alert is displayed on the display part.

18. The medical imaging apparatus according to claim 1, further comprising,
an adjustment acceptor for accepting adjustment of the real imaging slice position calculated by the real imaging slice position calculator as learning data, and
a learning part for analyzing the learning data being accepted and feeding the learning data back to the imaging slice parameter.

19. The medical imaging apparatus according to claim 1, further comprising,
a related position reference setter for setting as a standard related position, a related position of the imaging slice position, being independent of the imaging slice position, and generating a related position parameter from the standard related position being set, and
a real related position calculator for calculating a real related position as the related position in the imaging target subject, based on the related position parameter.

* * * * *